United States Patent [19]

Harada et al.

[11] Patent Number: 5,268,386
[45] Date of Patent: Dec. 7, 1993

[54] CERTAIN 3,4-DIHYDRO 4-OXOSPIRO [2H-1 BENZOPYRANS] USEFUL FOR TREATING HYPERURICEMIA

[75] Inventors: Hiroshi Harada, Toyonaka; Eiichi Ohsugi, Kawanishi; Yukio Yonetani, Nara; Toshihiro Shinosaki, Osaka, all of Japan

[73] Assignee: Shionogi & Co., Ltd., Osaka, Japan

[21] Appl. No.: 558,242

[22] Filed: Jul. 26, 1990

[30] Foreign Application Priority Data

Aug. 3, 1989 [JP] Japan .................................. 1-203024

[51] Int. Cl.$^5$ .................. C07D 311/22; C07D 339/02; A61K 31/385; A61K 31/35
[52] U.S. Cl. ................................... 514/456; 514/440; 549/32; 549/265; 549/401; 549/404; 549/408
[58] Field of Search ............... 549/401, 403, 406, 407, 549/408, 409, 410, 39, 331, 265, 32; 514/456, 440

[56] References Cited

U.S. PATENT DOCUMENTS

| | | | |
|---|---|---|---|
| 4,415,741 | 11/1983 | Kabbe | 549/345 |
| 4,479,007 | 10/1984 | Kabbe | 549/401 |
| 4,650,812 | 3/1987 | Cohen et al. | 514/456 |

FOREIGN PATENT DOCUMENTS

| | | | |
|---|---|---|---|
| 0248420 | 12/1987 | European Pat. Off. | 549/401 |
| 2148363 | 3/1973 | France | 549/401 |
| 1067986 | 5/1987 | United Kingdom | 549/401 |

OTHER PUBLICATIONS

DeBois et al., J. Med. Chem., 1981, 24, pp. 408–428.
Eiden et al., Chemical Abstracts, vol. 86 (1977), p. 525 Abstract No. 43585n.
Schmiz et al., Liebigs Ann. Der Chemie, 1980, pp. 2021–2029.
Eiden et al., Chemical Abstracts, vol. 92 (1980) p. 783 Abstract No. 41910q.
Chemical Abstracts, vol. 78, No. 19, Abstract 136075w, Phillippe, pp. 364–365, May 14, 1973.
Chemical Abstracts, vol. 86, No. 25, Abstract 189716c, Kabbe, pp. 590–591, Jun. 20, 1977.
Chemical Abstracts, vol. 87, No. 1, Abstract 5573y, DuBois, p. 448, Jul. 4, 1977.
Chemical Abstracts, vol. 97, No. 21, Abstract 182049f, Ertan, p. 791, Nov. 22, 1982.
Chemical Abstracts, vol. 108, No. 11, Abstract 94387e, Kitagawa, p. 644, Mar. 14, 1988.

Primary Examiner—Alan L. Rotman
Attorney, Agent, or Firm—Wenderoth, Lind & Ponack

[57] ABSTRACT

A novel heterocyclic compound capable of lowering the uric acid levels in plasma and urine having the formula (I):

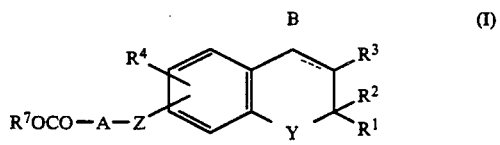

wherein $R^1$ and $R^2$ are independently hydrogen, lower alkyl, phenyl or substituted phenyl, or $R^1$ and $R^2$ may form a four- to eight-membered carbon ring together with the carbon atom to which they are attached; $R^3$ is hydrogen or lower alkyl; $R^4$ is one or two radicals selected from a group consisting of hydrogen, halogen, nitro, lower alkyl, phenyl, substituted phenyl, $-OR^5$ and $-SO_2NR^6R^{6'}$; $R^5$ is hydrogen, lower alkyl, phenyl-substituted lower alkyl, carboxymethyl or ester thereof, hydroxyethyl or ether thereof, or allyl; $R^6$ and $R^{6'}$ are independently hydrogen or lower alkyl; $R^7$ is hydrogen or a pharmaceutically active ester-forming group; A is a straight or branched hydrocarbon radical having one to five carbon atoms; B is halogen, oxygen, or dithiolane; Y is oxygen, sulfur, nitrogen or substituted nitrogen; Z is oxygen, nitrogen or substituted nitrogen; dotted line represents the presence or absence of a single bond.

5 Claims, No Drawings

CERTAIN 3,4-DIHYDRO 4-OXOSPIRO [2H-1 BENZOPYRANS] USEFUL FOR TREATING HYPERURICEMIA

BACKGROUND OF THE INVENTION

1. Field of the Invention

The present invention relates to novel compounds capable of inhibiting the biosynthesis of uric acid and also accelerating the excretion of said acid.

2. Prior Art

Hyperuricemia is a well known cause of gout, which is one of most popular diseases associated with the hyperuricemia, and the number of patients suffering from the gout is increasing. Hyperuricemia is also suggested to be a potential cause of certain angiopathys, such as ischemic cardiac disease and cerebrovascular disease. These diseases are associated with elevated level of uric acid in plasma and urine, and have been treated with medicines which lower the uric acid level.

There are two kinds of medicines used for such treatments. One is a xanthine oxidase inhibitor which inhibits the biosynthesis of uric acid The other is an eliminant which accelerates the excretion of uric acid. Examples of the inhibitor include Allopurinol and examples of the eliminant include Probenecid and Benzbromarone.

SUMMARY OF THE INVENTION

The present inventors have now discovered a class of heterocyclic compounds which can accelerate the excretion of uric acid and inhibit the biosynthesis of said acid through xanthine oxidase inhibition activity.

DETAILED DESCRIPTION

In particular, the present invention provides novel heterocyclic compounds of the formula (I)

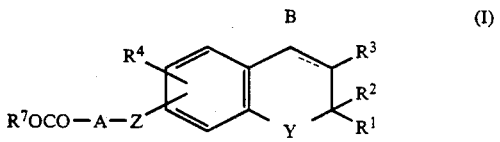

wherein $R^1$ and $R^2$ are independently hydrogen, lower alkyl, phenyl or substituted phenyl, or $R^1$ and $R^2$ may form a four- to eight-membered carbon ring together with the carbon atom to which they are attached; $R^3$ is hydrogen or lower alkyl; $R^4$ is one or two radicals selected from a group consisting of hydrogen, halogen, nitro, lower alkyl, phenyl, substituted phenyl, —$OR^5$ and —$SO_2NR^6R^{6'}$; $R^5$ is hydrogen, lower alkyl, phenyl-substituted lower alkyl, carboxymethyl or ester thereof, hydroxyethyl or ether thereof, or allyl; $R^6$ and $R^{6'}$ are independently hydrogen or lower alkyl; $R^7$ is hydrogen or a pharmaceutically active ester-forming group; A is a straight or branched hydrocarbon radical having one to five carbon atoms; B is halogen, oxygen, or ethylenedithio; Y is oxygen, sulfur, nitrogen or substituted nitrogen; Z is oxygen, nitrogen or substituted nitrogen; dotted line represents the presence or absence of a single bond.

As can be seen from the above formula (I), the compound of the invention can be classified into three groups, derivatives of chromanone (where Y is oxygen), thiochromanone (where Y is sulfur), and 2,3,4-tetrahydroquinoline (where Y is nitrogen).

For the purpose of the present invention, as disclosed and claimed herein, the following terms are defined as below.

The term "lower alkyl" refers to a straight or branched saturated hydrocarbon radical having one to five carbon atoms, including methyl, ethyl, n-propyl, isopropyl, butyl, isobutyl, sec-butyl, tert-butyl, pentyl, isopentyl, and the like.

The term "lower alkoxy" refers to those formed from lower alkyls noted above, including methoxy, ethoxy, propoxy, isopropoxy, butoxy, isobutoxy, pentoxy and the like.

The term "substituted phenyl" refers to phenyl substituted with halogen or lower alkyl, and the like. Examples of substituted phenyl include p-tolyl and p-chlorophenyl.

The term "four- to eight-membered carbon ring" refers to cyclobutyl, cyclopentyl, cyclohexyl, cycloheptyl,cyclooctyl, and the like.

The term "halogen atoms" refers to fluorine, chlorine, bromine, and iodine.

In the definition of $R^5$, the term "ester" used in the phrase "the ester of carboxymethyl" means a lower alkyl ester, such as methyl or ethyl ester; and the term "ether" used in the phrase "the ether of hydroxyethyl" means an ether which is formed by substitution of the hydrogen atom of hydroxyl group in the hydroxyethyl group by aliphatic or aromatic alkyl group, such as benzyl.

In the definition of $R^7$, the phrase "pharmaceutically active ester-forming group" refers to a group which binds to a carboxyl group through an ester bond. Such ester-forming groups can be selected from carboxy-protecting groups commonly used for the preparation of pharmaceutically active substances, especially prodrugs. For the purpose of the invention, said group should be selected from those capable of binding to compounds of formula (I) wherein $R^7$ is hydrogen through an ester bond. Resultant esters are effective to increase the stability, solubility, and absorption in gastrointestinal tract of the corresponding non-esterified forms of said compounds (I), and also prolong the effective blood-level of it. Additionally, the ester bond can be cleaved easily at the pH of body fluid or by enzymatic actions in vivo to provide a biologically active form of the compound (I). Preferred pharmaceutically active ester-forming groups include 1-(oxygen substituted)-$C_2$ to $C_{15}$ alkyl groups, for example, a straight, branched, ringed, or partially ringed alkanoyloxyalkyl groups, such as acetoxymethyl, acetoxyethyl, propionyloxymethyl, pivaloyloxymethyl, pivaloyloxyethyl, cyclohexaneacetoxyethyl, cyclohexanecarbonyloxycyclohexylmethyl, and the like, $C_3$ to $C_{15}$ alkoxycarbonyloxyalkyl groups, such as ethoxycarbonyloxyethyl, isopropoxycarbonyloxyethyl, isopropoxycarbonyloxypropyl, t-butoxycarbonyloxyethyl, isopentyloxycarbonyloxypropyl, cyclohexyloxycarbonyloxyethyl, cyclohexylmethoxycarbonyloxyethyl, bornyloxycarbonyloxyisopropyl, and the like, $C_2$ to $C_8$ alkoxyalkyls, such as methoxy methyl, methoxy ethyl, and the like, $C_4$ to $C_8$ 2-oxacycloalkyls such as, tetrahydropyranyl, tetrahydrofuranyl, and the like, substituted $C_8$ to $C_{12}$ aralkyls, for example, phenacyl, phthalidyl, and the like, $C_6$ to $C_{12}$ aryl, for example, phenyl xylyl, indanyl, and the like, $C_2$ to $C_{12}$ alkenyl, for example, allyl, (2-oxo-1,3-dioxolyl)methyl, and the like, and [4,5-dihydro-4-oxo-1H-pyrazolo[3,4-d]pyrimidin-1-yl]methyl, and the like.

The carboxy-protecting groups may be substituted in various ways. Examples of substituents include halogen atom, alkyl, alkoxy, alkylthio and carboxy groups.

The term "straight or branched hydrocarbon radical" in the definition of A refers to methylene, ethylene, propylene, methylmethylene, or isopropylene.

The substituent of the "substituted nitrogen" in the definition of Y and Z are hydrogen, lower alkyl, or acyl.

The term "phenyl-substituted lower alkyl" refers to a lower alkyl substituted with phenyl, such as benzyl, phenethyl or phenylpropyl.

Chromanone (I'), one of the compounds of the formula (I), wherein B, Y, and Z are oxygen, can be prepared according to the processes shown in Reaction Schemes 1 to 5 hereinafter described, using the compound (II) as the starting material. The compound (II) is described in the literature, and can be obtained by a well known method.

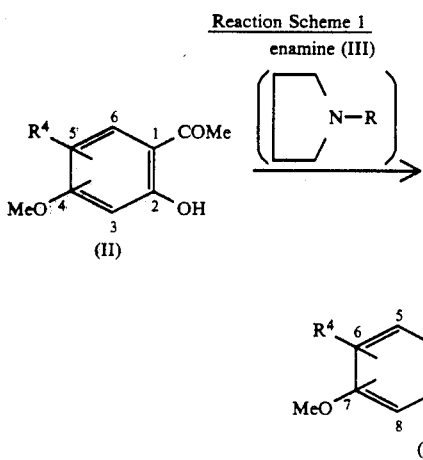

wherein R is a four- to eight-membered carbon ring having a double bond at the 1,2-position of the ring, or —C(Ph)=CH$_2$; R$^1$, R$^2$, and R$^4$ are as defined above.

In Reaction Scheme 1, the starting compound (II) is reacted with an enamine (III) to provide the compound (IV). The reaction is conducted in an organic solvent under nitrogen atmosphere at a temperature in the range of from about room temperature to the boiling point of the solvent, preferably from about 60° to about 80° C., for about 30 minutes to about 10 hours, preferably about 1 to about 7 hours. Organic solvents which may be used is dry alcohol, such as dry methanol, ethanol, and the like.

Enamines which may be used in the reaction include compounds of formula (III) wherein R is 1-cyclohexene or 1-cyclopentene, or —C(Ph)=CH$_2$. A selected enamine is used in an approximately equimolar to slightly excess amount relative to the compound (II).

When the reaction is complete, the mixture is distilled to remove the solvent, and the residue is treated by column chromatography, preferably silica gel column chromatography, using an appropriate eluent, for example, a mixture of ethyl acetate and hexane (1:2) or a mixture of ethyl acetate and dichloromethane (1:9 to 3:7). The eluate is concentrated to yield the compound (IV) as a thick syrup or a crude crystalline solid. The latter can be purified by recrystallization from a solvent, for example, a mixture of diethyl ether and hexane, a mixture of benzene and hexane, or a mixture of ethyl acetate and hexane.

The compound (IV) may be substituted with a lower alkyl group (—R$^3$) at the 3-position, if desired.

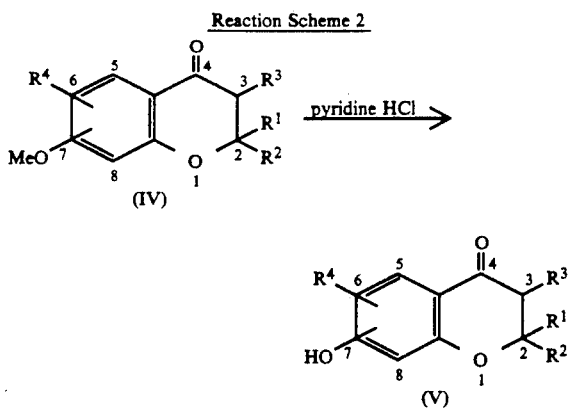

wherein R$^1$, R$^2$, R$^3$, and R$^4$ are as defined above.

In Reaction Scheme 2, the compound (IV) is reacted with pyridine hydrochloride to provide the compound (V).

The reaction is preferably conducted in dry pyridine hydrochloride at a temperature in the range of from about 150° to about 250° C., preferably from about 200° to about 220° C., for about 10 minutes to about 5 hours, preferably about 30 minutes to about one hour.

When the reaction is complete, water and diethyl ether are added to the reaction mixture, and the organic layer is separated. The organic solution is distilled to remove the ether. The residue is loaded on a silica gel column and eluted with an appropriate eluent, for example, a mixture of acetonitrile and dichloromethane (1:9 to 1:4), a mixture of ethyl acetate and dichloromethane (1:9), or diethyl ether. The eluate is concentrated to yield the compound (V) as a thick syrup or a crude crystalline solid. The latter can be purified by recrystallization from a solvent, such as a mixture of diethyl ether and hexane, diethyl ether, and the like.

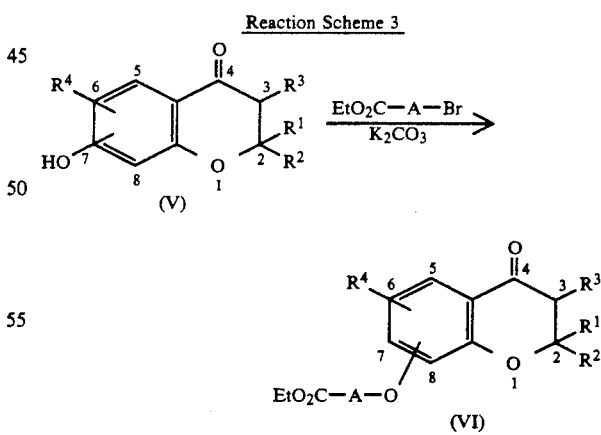

wherein R$^1$, R$^2$, R$^3$, R$^4$, and A are as defined above.

In Reaction Scheme 3, the compound (V) is reacted with an ethyl ester of haloganated carboxylic acid of the formula: EtO$_2$C-A-Br in the presence of a base under nitrogen atmosphere.

The reaction is preferably conducted in an organic solvent at a temperature in the range of from about 25° to about 100° C., preferably from about room temperature to the boiling point of the solvent for about 1 to about 48 hours, preferably about 2 to about 20 hours.

Prefered organic solvents are polar solvents which include acetonitrile, dimethylformamide (DMF) and acetone, and is more preferably DMF. Bases which may be used include alkali or alkaline earth metal carbonates. Prefered base is potassium carbonate. Ethyl esters of halogenated carboxylic acid which may be used include ethyl bromoacetate, ethyl bromopropionate, ethyl bromobutyrate, and the like. A selected ester is used in an approximately equimolar to slightly excess amount relative to the compound (V).

When the reaction is complete, the mixture is distilled to remove the solvent and the residue is extracted with diethyl ether. The ether extract is concentrated and the concentrate is subjected to recrystallization. Alternatively, the concentrate is treated by a silica gel column chromatography using an appropriate eluent, such as dichloromethane, a mixture of ethyl acetate and dichloromethane (1:9), or a mixture of ethyl acetate and hexane (1:2). The eluate is concentrated to yield the compound (VI) as a crude crystalline solid, which is then recrystallized from a solvent, for example, cyclohexane, a mixture of diethyl ether and hexane or a mixture of benzene and hexane.

Reaction Scheme 4

In Reaction Scheme 4, the compound (VI'), the same compound as the compound of formula (VI) wherein at lease one of the substituents represented by $R^4$ is a hydroxyl group, is reacted with an alkylating agent ($R^5X$) in the presence of a base to provide the compound (VII).

The reaction is preferably conducted in an appropriate organic solvent such as DMF at a temperature in the range of from about 25° to about 100° C., preferably from about room temperature to about 70° C. for about 1 to about 48 hours, preferably about 2 to about 20 hours.

Alkylating agents which may be used include methyl iodide, ethyl iodide, benzyl bromide, allyl bromide, isopropyl iodide, $PhCH_2O(CH)_2OTs$, and the like. Base can be selected from those commonly used in the alkylation reaction with a preference of potassium carbonate. When the alkylating agent is $PhCH_2O(CH)_2OTs$, sodium hydride is employed.

When the reaction is complete, the mixture is distilled to remove the solvent and the residue is extracted with diethyl ether. The ether extract is concentrated, and the concentrate is treated by a silica gel column chromatography. The compound (VII) is obtained as a thick syrup or a crude crystalline solid. Eluent which may be used is a mixture of ehtyl acetate and dichloromethane (1:9), a mixture of acetone and dichloromethane (1:99 to 1:20), or a mixture of acetonitrile and dichloromethane (1:4). Solvent which may be used for the recrystallization is diethyl ether, a mixture of ethyl acetate and hexane, or a mixture of diethyl ether and hexane.

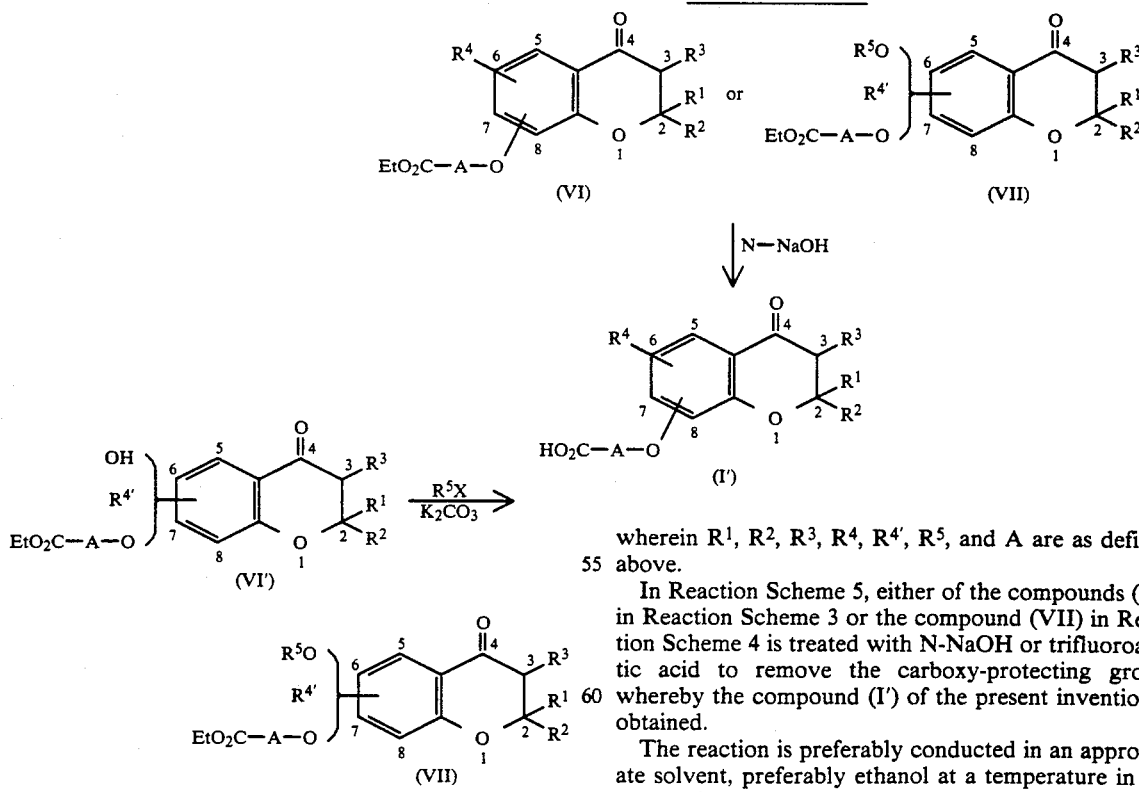

wherein $R^1$, $R^2$, $R^3$, and $R^5$, and A are as defined above, $R^{4'}$ is a radical selected from those listed in the definition of $R^4$ to the exclusion of a hydroxyl group, and X is halogen or -OTs.

wherein $R^1$, $R^2$, $R^3$, $R^4$, $R^{4'}$, $R^5$, and A are as defined above.

In Reaction Scheme 5, either of the compounds (VI) in Reaction Scheme 3 or the compound (VII) in Reaction Scheme 4 is treated with N-NaOH or trifluoroacetic acid to remove the carboxy-protecting group, whereby the compound (I') of the present invention is obtained.

The reaction is preferably conducted in an appropriate solvent, preferably ethanol at a temperature in the range of from about 10° C. to the boiling point of the solvent for about 10 minutes to about 48 hours, preferably about 30 minutes to about 20 hours.

When the reaction is complete, the mixture is made acid with hydrochloric acid and concentrated. The residue is then recrystallized from an appropriate solvent, for example, diethyl ether, ethanol, ethylacetate, acetone, a mixture of ethanol and water, a mixture of diethyl ether and hexane, a mixture of ethyl acetate and hexane, a mixture of acetone and hexane, or a mixture of acetone, ethyl acetate and diethyl ether.

The resulting compound (I') in carboxylic acid form ($R^7$ in the formula (I) is hydrogen) can be converted easily into pharmaceutically active ester to yield a pro-drug as mentioned above. Examples of pharmaceutically active esters are those formed with ester-forming groups listed above, including pivaloyloxymethyl, phtalidyl, 1-hydroxymethylallopurinol, and the like. Esterification can be carried out using standard procedures well known to those skilled in the art.

In the above description, only chromanone derivatives are illustrated. However, one skilled in the art will readily appreciate that other class of compounds of the formula (I), thiochromanones and quinolines, can be synthesized substantially in accordance with the Reaction Scheme illustrated above just by replacing the starting material (II) with a corresponding compound having a thioalcohol group (—SH) or amino group (—$NH_2$) instead of a hydroxyl group (—OH) in the formula (II).

The compounds of the formula (I) have been shown to accelerate the excretion of uric acid, and also inhibit the biosynthesis of uric acid through xanthine oxidase inhibitory activity as illustrated in the Experiments hereinafter described. Therefore, the compounds of the invention are useful for the treatment of various diseases associated with hyperuricemia, for example, gout, ischemic cardiac disease, and cerebrovascular disease.

The following Examples further illustrate the compounds of the present invention and methods for their synthesis. The Examples are not intended to be limiting to the scope of the invention in any respect and should not be so construed.

Preparation 1

(4',6'-Dimethoxy-2'-hydroxy-3'-methylphenyl) ethanone

A mixture of 2,4,6-trimethoxytoluene (90% purity, 9.1 g, 45 mmol), acetyl chrolide (3.9 ml, 55 mmol), anhydrous aluminium chloride (7.98 g, 60 mmol), and anhydrous dichloromethane is stirred for 3 hours while cooling on ice.

The reaction mixture is then poured into ice-cooled water and the mixture is extracted with dichloromethane. The organic layer is separated and washed with water, dried, and concentrated to yield an oil. The oil is loaded onto a Lober column (Merck) and eluted with a mixture of acetyl chloride and dichloromethane (1:9).

From earlier fractions, the starting materials are recovered. From succeeding fractions, a crystalline solid is obtained (5.8 g, m.p.=102°-103° C.).

To a solution of the crystalline solid (5.2 g, 23 mmol) in dry dichloromethane (23 ml) is added dropwise a 2M boron trichloride solution in dichloromethane (25 ml, 50 mmol) at −50° C. The reaction mixture is stirred at −50° to −20° C. for 2 hours and then −20° C. to room temperature for 2 hours. Ice-cooled water is added to the mixture and stirring is continued overnight at room temperature. The resulting mixture is extracted with dichloromethane, and the extract is washed with water, and concentrated to yield a crystalline residue. The residue is washed with diethyl ether to obtain the title compound as a crystalline solid (4.18 g, m.p.=143°-144° C., yield 49.3%, based on the starting compound). Recrystallization from ethyl acetate gives a product having a melting point of 146°-147° C.

Elementaly analysis (for $C_{11}H_{14}O_4$)
Calcd.: C, 62.85; H, 6.71
Found: C, 62.53; H, 6.68
$^1$H-NMR (CDCl$_3$) δppm: 14.0(1H,s), 5.93(1H, s), 3.89(6H,s), 2.60(3H,s), 2.00(3H,s).
$^{13}$C-NMR (CDCl$_3$) δppm: 203.3, 163.68, 163.49, 105.73,
105.54, 85.6, 55.4, 55.3, 33.1,
7.1

Preparation 2

(2'-Chloro-6'-hydroxy-4'-methoxyphenyl)ethanone

To a solution of 3,5-dimethoxychlorobenzene (5.18 g, 30 mmol) and acetyl chloride (2.59 g, 33 mmol) in dry dichloromethane (30 ml) is added anhydrous aluminium chloride (4.4 g, 33 mmol) by portions at −15° to −10° C. and the mixture is stirred for 3 hours at the same temperature. The resulting reaction mixture is poured into ice-cold dilute hydrochloric acid, and the solution is extracted with dichloromethane. The organic layer is separated and washed with saturated brine, dried and concentrated. The residue is placed on a silica gel column and eluted with a mixture of hexane and ethyl acetate (2:1) to obtain an oil (5.25 g). To a solution of the oil (4.75 g, 20 mmol) in dry dichloromethane (22 ml) is added dropwise a 2M boron trichloride solution in dichloromethane (24.2 ml, 48.4 mmol), at −50° to −60° C.

After stirring the mixture at −50° to −30° C. for 1 hour, ice-cold water is added thereto. The resulting mixture is extracted with dichloromethane, and the organic layer is washed with saturated brine, dried and concentrated. A crystalline residue is recrystallized from hexane to obtain the title compound (3.91 g, yield 72.1%, based on the starting compounds, m.p.=54° to 55° C.).

$^1$H-NMR (CDCl$_3$) δppm: 13.47(1H,s), 6.55(1H, d, J=2.6),
6.37(1H,d, J=2.6), 3.83(3H,s),
2.81(3H,s).

Preparation 3

6-Methoxyspiro[2H-1-benzopyran-2,1'-cyclohexan]-4(3H)-one

A solution of (2'-hydroxy-5'methoxyphenyl)ethanone (3.32 g, 20 mmol) and cyclohexanonepyrrolidine (enamine form) (3.18 g, 21 mmol) in dry ethanol (40 ml) is heated to reflux for 1.5 hours under nitrogen gas. The solvent is removed by distillation, and the residue is dissolved in diethyl ether, washed with dilute HCl and then water, dried, and concentrated. The residue is placed on a silica gel column and eluted with a mixture of ethyl acetate and hexane (1:2) to obtain the title compound as thick syrup (4.5 g, yield 91.3%).

Preparations 4-11

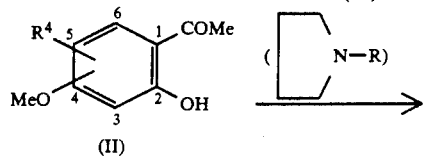

In Preparations 4–11, corresponding compounds (IV) were prepared according to the procedure of Preparation 3 employing the starting materials (II) and reaction conditions shown in Table 1. Physicochemical properties of each product are given in Table 2. The term "starting material" refers to the compound used in the reaction. Said compound is depicted by the number of Preparation or literature which gives or discloses the same.

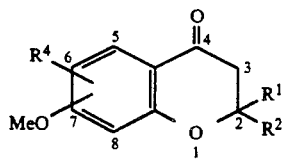

(IV)

TABLE 1

| Compd. of Prep. No. | (II) material | position of —OMe | $R^4$ | mmol | (III) R | mmol | Reaction conditions MeOH (ml) | Time (hr) | Columnchromato Eluent | (IV) $R^1$ | $R^2$ |
|---|---|---|---|---|---|---|---|---|---|---|---|
| 3 | a) | 5 | H | 20 | 1-cyclohexene | 21 | 40 | 1.5 | ethyl acetate-hexane 1:2 | —(CH$_2$)$_5$— | |
| 4 | b) | 4 | H | 10 | 1-cyclohexene | 11 | 25 | 1 | ethyl acetate-dichloro methane 1:9 | —(CH$_2$)$_5$— | |
| 5 | c) | 4 | 3-OMe | 20 | 1-cyclohexene | 22 | 40 | 1 | — | —(CH$_2$)$_5$— | |
| 6 | d) | 4 | 6-OMe | 10 | —C(Ph)=CH$_2$ | 12 | 30 | 7 | ethyl acetate-dichloro methane 1:9–3:7 | Me | Ph |
| 7 | d) | 4 | 6-OMe | 10 | 1-cyclopentene | 10 | 30 | 1 | ethyl acetate-dichloro methane 1:9 | —(CH$_2$)$_4$— | |
| 8 | d) | 4 | 6-OMe | 10 | 1-cyclohexene | 12 | 25 | 0.7 | ethyl acetate-dichloro methane 1:9 | —(CH$_2$)$_5$— | |
| 9 | e) | 4 | 6-Me | 10 | 1-cyclohexene | 11 | 25 | 1 | ethyl acetate-dichloro methane 1:9 | —(CH$_2$)$_5$— | |
| 10 | f) | 4 | 6-OMe 3-Me | 10 | 1-cyclohexene | 11 | 25 | 1 | ethyl acetate-dichloro methane 1:9 | —(CH$_2$)$_5$— | |
| 11 | g) | 4 | 6-Cl | 19 | 1-cyclohexene | 21 | 48 | 1.5 | ethyl acetate-hexane | —(CH$_2$)$_5$— | |

| Compd. of Prep. No. | (IV) $R^4$ | position of —OMe | Yield (%) |
|---|---|---|---|
| 3 | H | 6 | 91 |
| 4 | H | 7 | 87 |
| 5 | 8-OMe | 7 | 61 |
| 6 | 5-OMe | 7 | 20 |
| 7 | 5-OMe | 7 | 76 |
| 8 | 5-OMe | 7 | 92 |
| 9 | 5-Me | 7 | 60 |
| 10 | 5-OMe 8-Me | 7 | 76 |
| 11 | 5-Cl | 7 | 56 | a) St. v. Kostanecki and V. Lampe, Chem. Ber., 37, 773 (1904)
b) Y. Tahara, Chem. Ber., 24, 2459 (1891)
c) E. David and St. v. Kostanecki, Chem. Ber., 36, 125 (1903)
d) St. v. Kostanecki and J. Tambor, Chem. Ber., 32, 226 (1899)
e) J. Tambor, Chem. Ber., 41, 793 (1908)
f) Preparation 1
g) Preparation 2

TABLE 2

| Compd. of Prep. No. | M. p. (recrystallized) | Molecular formula | Elemental analysis C | H | Cl | $^1$H-NMR(CDCl$_3$) δ ppm (J Hz) |
|---|---|---|---|---|---|---|
| 3 | thick syrup | | | | | 7.30(1H, d, J=2.5), 7.10(1H, dd, J=9.0 and 2.5), 6.86(1H, d, J=9.0), 3.78(3H, s), 2.66(2H, s), 2.1–1.3(10H, m) |
| 4 | thick syrup | | | | | 7.78(1H, d, J=9.0), 6.50(1H, dd, J=9.0 and 2.0), 6.40(1H, d, J=2.0), 3.82(3H, s), 2.63(2H, s), 2.2–1.2(10H, m) |
| 5 | 78–79 ether-hexane | | | | | 7.64(1H, d, J=9.0), 6.10(1H, d, J=9.0), 3.92(6H, s), 6.77(2H, s), 2.3–1.2(10H, m) |
| 6 | 137–138 benzene-hexane | C$_{18}$H$_{18}$O$_4$ | 72.47 (72.51) | 6.13 (6.28) | | 7.5–7.1(5H, s), 6.19(1H, d, J=2.0), 5.97(1H, d, J=2.0), 3.81 (3H, s), 3.78(3H, s), 3.20(1H, d, J=16.5), 2.95(1H, d, J=16.5), 1.70(3H, s) |
| 7 | thick syrup | | | | | 6.03(2H, s), 3.88(3H, s), 3.82(3H, s), 2.73(2H, s), 2.2–1.4(8H, m) |
| 8 | 115–116 ether-hexane | C$_{16}$H$_{20}$O$_4$ | 69.54 (69.55) | 7.30 (7.23) | | 6.07(1H, d, J=2.0), 6.00(1H, d, J=2.0), 3.85(3H, s), 3.80 (3H, s), 2.61(2H, s), 2.0–1.3(10H, m) |
| 9 | thick syrup | | | | | 6.30(2H, s), 3.80(3H, s), 2.61(s) and 2.58(s)(5H), 2.2–1.2 (10H, m) |
| 10 | 174–175 ether-hexane | | | | | 6.09(1H, s), 3.90(6H, s), 2.60(2H, s), 2.05–1.2(13H, m) |

TABLE 2-continued

| Compd. of Prep. No. | M. p. (recrystallized) | Molecular formula | Elemental analysis | | | $^1$H-NMR(CDCl$_3$) δ ppm (J Hz) |
|---|---|---|---|---|---|---|
| | | | C | H | Cl | |
| 11 | 83–84 ethyl acetate-hexane | C$_{15}$H$_{17}$ClO$_3$ | 64.17 (63.92) | 6.10 (6.15) | 12.63 (12.52) | 6.57(1H, d, J=2.4), 6.78(1H, d, J=2.4), 3.83(3H, s), 2.68 (2H, s), 2.0–1.25(10H, m) |

Preparation 12

5,6-Dichloro-7-methoxyspiro[2H-1-benzopyran-2,1'-cyclohexan]-4(3H)-one (12-1) and 5,8-dichloro-7-methoxyspiro[2H-1-benzopyran-2,1'-cyclohexan]-4(3H)-one (12-2)

To a solution of 5-chloro-7-methoxyspiro[2H-1-benzopyran-2,1'-cyclohexan]-4(3H)-one (prepared in Preparation 11) (0.63 g, 2.25 mmol) in dry dichloromethane (10 ml) is added dropwise a solution of sulfuryl chloride (0.345 g, 2.56 mmol) in dichloromethane (4.5 ml) at −35° to −30° C. over 10 minutes. The mixture is then continuously stirred at a temperature ranging from −30° to −20° C. for half an hour, at 0° to 3° C. for one hour, and 3° C. to room temperature for half an hour. The solvent is removed and the residue is treated with diethyl ether. The mixture is filtered to obtain the crystalline compound (compound No. 12-1) (0.375 g, yield 53%, m.p.=167°–168° C.).

The filtrate is concentrated and the residue is diluted with hexane. The resulting precipitate is collected by filteration to yield a mixture of crystalline compound (12-1) and compound (12-2) (0.22 g, m.p.=109°–112° C., (12-1):(12-2)=1:3). Recrystallization from ethyl acetate gives a pure compound (12-2) having a melting point of 126° to 127° C.

Compound (12-1)

Elemental analysis (for C$_{15}$H$_{16}$Cl$_2$O$_3$)
Calcd.: C, 57.16; H, 5.12; Cl, 22.49
Found: C, 57.16; H, 5.09; Cl, 22.53
$^1$H-NMR (CDCl$_3$) δppm: 6.47(1H,s), 3.95(3H,s), 2.70(2H,s), 2.0–1.25(10H,m).
$^{13}$C-NMR (CDCl$_3$) δppm: 188.69, 160.63, 160.27, 133.22,
117.03, 112.35, 99.87, 80.46,
56.7, 48.82, 34.60, 25.06, 21.46

Compound (12-2)

Elemental analysis (for C$_{15}$H$_{16}$Cl$_2$O$_3$)
Calcd.: C, 57.16; H, 5.12; Cl: 22.49
Found C, 57.26; H, 5.08; Cl, 22.50
$^1$H-NMR (CDCl$_3$) δppm: 6.65(1H,s), 3.97(3H,s), 2.70(2H,s), 2.2–1.1(10H,m).
$^{13}$C-NMR (CDCl$_3$) δppm: 189.2, 159.4, 157.32, 133.48,
112.97, 109.87, 107.97, 81.25,
56.68, 49.30, 34.71, 25.15,
21.37

Preparation 13

5,7-Dimethoxy-3-methylspiro[2H-1-benzopyran-2,1'-cyclohexan]-4(3H)-one

A solution of 5,7-dimethoxyspiro[2H-1-benzopyran-2,1'-cyclohexan]-4(3H)-one (prepared in Preparation 8) (1.38 g, 5 mmol) in dry tetrahydrofuran (10 ml) is added dropwise at −78° C. to a solution of lithium diisopropylamide (prepared from diisopropylamine (0.77 ml, 7.6 mmol) and 1.3N butyl lithium solution in hexane (3.85 ml, 5.0 mmol)) in tetrahydrofuran. To the mixture is added hexamethyl phosphoric triamide (1.05 ml) and then a solution of methyl iodide (0.78 g, 5.5 mmol) in tetrahydrofuran (1 ml) at −70° C. After the mixture is reacted at −78° to 0° C. for 2.5 hours and then at 0° to 3° C. for 2 hours, an aqueous solution of ammonium chloride is added thereto. The mixture is then extracted with diethyl ether and the organic layer is separated, washed twice with saturated brine, dried and the solvent is removed by distillation. The residue is loaded onto a Lober column and eluted with a mixture of acetonitrile and dichloromethane (1:9) to obtain the title compound as an oil (1.01 g, yield 69.6%).

$^1$H-NMR (CDCl$_3$) δppm: 6.08(1H,d,J=2), 6.02(1H,d,J=2),
3.87(3H,s), 3.83(3H,s),
2.51(1H,q,J=7), 2.1–1.3(10H,m),
1.13(3H,d,J=7).

Preparation 14

6-Hydroxyspiro[2H-1-benzopyran-2,1'-cyclohexan]-4(3H)-one

A mixture of 6-methoxyspiro[2H-1-benzopyran-2,1'-cyclohexan]-4(3H)-one (prepared in Preparation 3) (1.0 g, 4.06 mmol) in dry pyridine HCl (6 g, 52 mmol) is heated to 210°–215° C. on an oil bath for 45 minutes with stirring, and allowed to cool. The mixture is extracted with water and diethyl ether. The ether layer is separated, washed with dilute hydrochrolic acid and then water, dried and concentrated. The residue is placed on a silica gel column and eluted with a mixture of acetonitrile and dichloromethane (1:9 to 1:4) to obtain the title compound as an oil (0.81 g, yield 85.5%).

Preparation 15–25

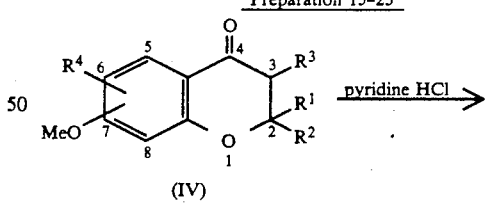

(IV)

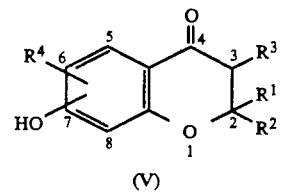

(V)

In Preparations 15 to 25, corresponding compounds (V) are prepared substantial in accordance with procedures described in Preparation 14 using starting materials (IV) and reaction conditions shown in Table 3. Physicochemical properties of each product are given in Table 4.

TABLE 3

| Compd. of Prep. No. | (IV) pyridine material | mmol | HCl (mmol) | reaction conditions Temp (°C.) | Time (hr.) | Chromato Eluent | (V) R¹ | R² | R³ | R⁴ | position of —OMe | Yield (%) |
|---|---|---|---|---|---|---|---|---|---|---|---|---|
| 14 | 3 | 4.06 | 52 | 210–215 | 0.8 | acetonitrile-dichloromethane 1:9–1:4 | —(CH$_2$)$_5$— | | H | H | 6 | 86 |
| 15 | 4 | 7.0 | 100 | 210–220 | 1 | ethyl acetate-dichloro methane 1:9 | —(CH$_2$)$_5$— | | H | H | 7 | 92 |
| 16 | 5 | 10.87 | 156 | 210–215 | 1 | — | —(CH$_2$)$_5$— | | H | 8-OH | 7 | 81 |
| 17 | 6 | 3.1 | 31 | 200–215 | 0.7 | ether | Me | Ph | H | 5-OH | 7 | 78 |
| 18 | 7 | 7.62 | 103 | 210–220 | 1 | ethyl acetate-dichloro methane 1:9 | —(CH$_2$)$_4$— | | H | 5-OH | 7 | 80 |
| 19 | 8 | 10.7 | 110 | 210–220 | 1 | ether | —(CH$_2$)$_5$— | | H | 5-OH | 7 | 97 |
| 20 | 9 | 6.0 | 81 | 210–220 | 1 | ethyl acetate-dichloro methane 1:9 | —(CH$_2$)$_5$— | | H | 5-Me | 7 | 71 |
| 21 | 10 | 6.0 | 81 | 210–220 | 1 | ethyl acetate-dichloro methane 1:9 | —(CH$_2$)$_5$— | | H | 5-OH 8-Me | 7 | 76 |
| 22 | 11 | 5.34 | 65 | 210–215 | 1 | ethyl acetate-dichloro methane 1:9 | —(CH$_2$)$_5$— | | H | 5-Cl | 7 | 67 |
| 23 | 12-1 | 1.59 | 43 | 210 | 0.5 | ethyl acetate-dichloro methane 1:9 | —(CH$_2$)$_5$— | | H | 5-Cl 6-Cl | 7 | 79 |
| 24 | 12-2 | 2.6 | 35 | 205–215 | 0.5 | — | —(CH$_2$)$_5$— | | H | 5-Cl 8-Cl | 7 | 49 |
| 25 | 13 | 7.6 | 103 | 210–220 | 1 | ethyl acetate-dichloro methane 1:9 | —(CH$_2$)$_5$— | | Me | 5-OH | 7 | 96 |

TABLE 4

| Compd. of Prep. No. | M. p. (°C.) (recrystallized) | Molecular formula | Elemental analysis (found) C | H | Cl | ¹H-NMR(CDCl$_3$) δ ppm (J Hz) |
|---|---|---|---|---|---|---|
| 14 | thick syrup | | | | | 7.40(1H, d, J=2.5), 7.10(1H, dd, J=9.0 and 2.5), 6.85(1H, d, J=9.0), 6.85(1H, b), 2.68(2H, s), 2.1–1.2(10H, m) |
| 15 | 171–172 | | | | | 7.90(1H, s), 7.79(1H, d, J=9.0), 6.54(1H, dd, J=9.0 and 2.0), 6.44(1H, d, J=2.0), 2.68(2H, s), 2.2–1.2(10H, m) |
| 16 | 83–84 ether-hexane | C$_{14}$H$_{18}$O$_4$ | 67.73 (67.60) | 6.50 (6.82) | | 7.43(1H, d, J=9.0), 6.73(1H, s), 6.60(1H, d, J=9.0), 5.83(1H, s), 2.71(2H, s), 2.2–1.3(10H, m) |
| 17 | thick syrup | | | | | 7.5–7.2(5H, m), 6.05(1H, d, J=2.0), 5.88(1H, d, J=2.0), 3.30(1H, d, J=16.5), 3.03(1H, d, J=16.5), 1.70(3H, s) |
| 18 | thick syrup | | | | | 11.97(1H, s), 7.50(1H, bs), 5.96(1H, d, J=2.0), 5.89(1H, d, J=2.0), 2.78(2H, s), 2.2–1.5(8H, m) |
| 19 | 140–141 ether | C$_{14}$H$_{18}$O$_4$ | 67.73 (67.73) | 6.50 (6.52) | | 11.97(1H, s), 7.68(1H, s), 5.95(1H, s), 2.65(2H, s), 2.1–1.2(10H, m) |
| 20 | 171–172 | | | | | 7.57(1H, s), 6.34(2H, s), 2.66(s) and 2.60(s)(5H), 2.1–1.3(10H, m) |
| 21 | 179–180 | | | | | in acetone-d$_6$ 6.00(1H, s), 3.1(2H, b), 2.65(2H, s), 2.0(3H, s), 2.2–1.1(10H, m) |
| 22 | 188–189 ether-hexane | C$_{14}$H$_{15}$ClO$_3$ | 63.04 (63.02) | 5.67 (5.70) | 13.29 (13.10) | 6.84(1H, s), 6.58(1H, d, J=2.4), 6.39(1H, d, J=2.4), 2.7(2H, s), 2.0–1.25(10H, m) |
| 23 | 189–191 | C$_{14}$H$_{14}$Cl$_2$O$_3$ | 55.83 (55.73) | 4.69 (4.74) | 23.54 (23.53) | 6.60(1H, s), 6.23(1H, b), 2.68(2H, s), 2.05–1.15(10H, m) |
| 24 | thick syrup | | | | | 6.78(1H, s), 6.60(1H, bs), 2.72(2H, s), 2.1–1.1(10H, m) |
| 25 | thick syrup | | | | | 12.0(1H, s), 7.3(1H, bs), 5.95(2H, bs), 2.54(1H, q, J=7.0), 2.1–1.1(10H, m), 1.19(3H, d, J=7.0) |

Preparation 26

5,7-dihydroxyspiro[2H-1-benzopyran-2,1'-cyclohexan]-4(3H)-one

A mixture of 5,7-dimethoxyspiro[2H-1-benzopyran-2,1'-cyclohexan]-4(3H)-one [H.F.Birch, A.Robertson, and T.S.Subramanjam, J.Chem.Soc., 1832 (1936)] (1.3 g, 6.25 mmol) and 48% hydrobromic acid (50 ml) is heated to reflux for one hour. After cooling, the reaction mixture is concentrated under reduced pressure. The concentrate is extracted with diethyl ether and the extract is washed with water, dried, and concentrated. The residue is placed on a silica gel column and eluted with diethyl ether. The eluate is treated with ether to yield the title compound as a crystalline solid (0.65 g, 58%).

¹H-NMR (d$_6$-acetone) δppm: 5.92(2H,s),
4.46(2H,t,J=6.5),
3.16(2H,s),
2.75(2H,t,J=6.5).

Preparation 27

Ethyl [(3,4-dihydro-4-oxospiro[2H-1-benzopyran-2,1'-cyclohexan]-6-yl)oxy]acetate A mixture of 6-hydroxy-spiro[2H-1-benzopyran-2,1'-cyclohexan]-4(3H)-one (prepared in Preparation 14) (0.878 g, 3.78 mmol), ethyl bromoacetate (0.69 g, 4.13 mmol), anhydrous potassium carbonate (0.78 g, 5.65 mmol) and dry N,N-dimethylformamide (DMF) (7.5 ml) is stirred at room temperature for 4 hours under nitrogen gas. DMF is removed by distillation under reduced pressure and the residue is extracted with diethyl ether. The ether layer is separated and washed successively with water, dilute sodium hydroxide and saturated brine, dried and distilled to remove ether. The residue is recrystallized from cyclohexane to obtain the title compound as a crystalline solid (1.11 g, yield 92.5%, m.p=72°–73° C.).

Preparation 28-44

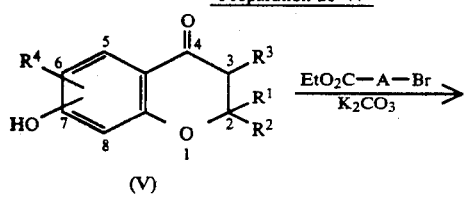
(V)

$\xrightarrow{\text{EtO}_2\text{C}-\text{A}-\text{Br}}{\text{K}_2\text{CO}_3}$

-continued
Preparation 28-44

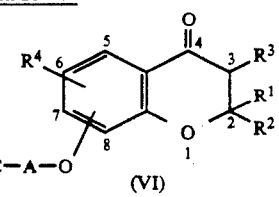
(VI)

In Preparations 28 to 44, corresponding compounds (VI) were prepared according to the procedure of Preparation 27 employing the starting materials (V) and reaction conditions given in Table 5. Purification was conducted by means of silica gel column chromatography. Physicochemical properties of each product are shown in Table 6.

TABLE 5

| Compd. of Prep. No. | V material | mmol | Ethyl bromoacetate (mmol) | Potassium carbonate (mmol) | CH₃CN (ml) | Reaction conditions Temp. (°C.) | Time (hrs.) | Chromato Eluent | VI R¹ | R² | R³ |
|---|---|---|---|---|---|---|---|---|---|---|---|
| 27 | 14 | 3.78 | 4.13 | 5.65 | 7.5 | 25 | 4 | — | —(CH₂)₅— | | H |
| 28 | 15 | 6.0 | 6.0 | 9.0 | 18 | 25 | 4 | ethyl acetate-dichloromethane 1:9 | —(CH₂)₅— | | H |
| 29 | 17 | 2.7 | 2.7 | 4.1 | 8 | 25 | 20 | ethyl acetate-dichloromethane 1:9 | Me | Ph | H |
| 30 | 18 | 6.0 | 6.0 | 9.0 | 18 | 25 | 4 | ethyl acetate-dichloromethane 1:9 | —(CH₂)₄— | | H |
| 31 | 19 | 9.03 | 9.03 | 15 | 27 | 25 | 20 | ethyl acetate-dichloromethane 1:9 | —(CH₂)₅— | | H |
| 32 | 19 | 4.03 | 9.3 | 10 | 15 (DMF) | 25 | 2.5 | dichloromethane | —(CH₂)₅— | | H |
| 33 | 25 | 6.0 | 6.0 | 9.0 | 18 | 25 | 4 | ethyl acetate-dichloromethane 1:9 | —(CH₂)₅— | | H |
| 34 | 20 | 6.0 | 6.0 | 9.0 | 18 | 25 | 4 | ethyl acetate-dichloromethane 1:9 | —(CH₂)₅— | | H |
| 35 | 21 | 6.0 | 6.0 | 9.0 | 18 | 25 | 4 | ethyl acetate-dichloromethane 1:9 | —(CH₂)₅— | | H |
| 36 | 22 | 3.52 | 3.87 | 5.3 | 9 (acetone) | reflux | 2 | ethyl acetate- 1:2 | —(CH₂)₅— | | H |
| 37 | 23 | 1.26 | 1.5 | 1.9 | 6 | 25 | 20 | ethyl acetate-hexane 1:2 | —(CH₂)₅— | | H |
| 38 | 24 | 1.26 | 1.5 | 1.9 | 6 | 25 | 20 | ethyl acetate-hexane 1:3 | —(CH₂)₅— | | H |
| 39 | 26 | 4.66 | 4.66 | 7.0 | 14 | 25 | 16 | — | H | H | H |
| 40 | a) | 6.64 | 6.97 | 10 | 20 | 25 | 20 | — | H | H | H |
| 41 | b) | 7.0 | 7.32 | 10.5 | 20 | 25 | 20 | — | Me | Me | H |
| 42 | c) | 7.0 | 7.32 | 10.5 | 20 | 25 | 20 | — | H | Me | H |
| 43ƒ) | d) | 2.51 | 2.76ᵍ) | 5.0 | 5 | 25 | 3 | ethyl acetate-dichloromethane 1:9 | H | Ph | H |
| 44 | e) | 11.53 | 11.64 | 17.39 | 34 | 25 | 16 | ethyl acetate-dichloromethane 1:9 | Me | Me | H |

| Compd. of Prep. No. | R⁴ | VI position of —OCH₂COOEt | Yield (%) |
|---|---|---|---|
| 27 | H | 6 | 93 |
| 28 | H | 7 | 98 |
| 29 | 5-OH | 7 | 84 |
| 30 | 5-OH | 7 | 79 |
| 31 | 5-OH | 7 | 86 |
| 32 | 5-OCH₂COOEt | 7 | 91 |
| 33 | 5-OH | 7 | 87 |
| 34 | 5-Me | 7 | 96 |
| 35 | 5-OH 8-Me | 7 | 91 |

TABLE 5-continued

| | | | |
|---|---|---|---|
| 36 | 5-Cl | 7 | 82 |
| 37 | 5-Cl 6-Cl | 7 | 90 |
| 38 | 5-Cl 8-Cl | 7 | 63 |
| 39 | 5-OH | 7 | 80 |
| 40 | H | 7 | 100 |
| 41 | H | 7 | 98 |
| 42 | H | 7 | 93 |
| 43[f] | H | 7 | 85 |
| 44 | 5-OH | 7 | 88 | a) P. Naylor, G. R. Ramage and F. Schofield, J. Chem. Soc., 1190 (1958). $R^1$, $R^2$, $R^3$, $R^4$; H, position of —OH; 7-position.
b) J. Arima, J. Chem. Soc. Japan, 53, 715 (1932). D. Sowmithran, and K. J. R. Prasad, Synthesis, 545 (1985). $R^1$, $R^2$; Me $R^3$, $R^4$; H, position of —OH; 7-position
c) M. Miyano and M. Matsui, Bull. Chem. Soc. Japan, 31, 397 (1958). $R^1$, $R^3$, $R^4$; H, position of —OH; 7-position $R^2$; Me
d) Y. Tatsuta, J. Chem. Soc., Japan, 61, 752 (1940). $R^1$, $R^3$, $R^4$; H, position of —OH; 7-position $R^2$; Ph
e) F. Camps, J. Coll, A. Messegner, M. A. Pericas, S. Ricart, W. S. Bowers and D. M. Soderland, Synthesis, 725 (1980). $R^1$, $R^2$; Me $R^3$; H $R^4$; 5-OH, position of —OH; 7-position
f) t-Butyl ester
g) t-Butyl bromoacetate

TABLE 6

| Compd. of Prep. No. | M. p. °C. (recrystallized) | Molecular formula | Elemental analysis (found) | | $^1$H-NMR CDCl$_3$ δ ppm (J Hz) |
|---|---|---|---|---|---|
| | | | C | H | |
| 27 | 72–73 cyclohexane | $C_{18}H_{22}O_5$ | 67.91 (67.85) | 6.96 (7.07) | 7.23–7.10(2H, m), 6.90(1H, d, J=9.0), 4.58(2H, s), 4.26(2H, q, J=7.0), 2.65(2H, s), 2.1–1.2(13H, m) |
| 28 | 66 cyclohexane | $C_{18}H_{22}O_5$ | 67.91 (67.70) | 6.96 (7.14) | 7.81(1H, d, J=9.0), 6.56(1H, dd, J=9.0 and 2.5), 6.40(1H, d, J=2.5), 4.66(2H, s), 4.28(2H, q, J=7.0), 2.67(2H, s), 2.2–1.2(10H, m), 1.31(3H, t, J=7.0) |
| 29 | 138.5–139.5 benzene-hexane | $C_{20}H_{20}O_6$ | 67.40 (67.50) | 5.66 (5.73) | 11.8(1H, s), 7.5–7.2(5H, m), 6.1(1H, d, J=2.2), 5.90(1H, d, J=2.2), 4.60(2H, s), 4.25(2H, q, J=7.0), 3.26(1H, d, J=16.5), 3.00(1H, d, J=16.5), 1.70(3H, s), 1.26(3H, t, J=7.0) |
| 30 | thick syrup | | | | 12.0(1H, s), 5.95(2H, s), 4.61(2H, s), 4.29(2H, q, J=6.0), 2.79(2H, s), 2.3–1.5(8H, m), 1.30(3H, t, J=6.0) |
| 31 | 70–71 | | | | 11.98(1H, s), 5.98(2H, s), 4.61(2H, s), 4.27(2H, q, J=7.0), 2.65(2H, s), 2.1–1.2(13H, m) |
| 32 | 87–88 ethyl acetate-hexane | $C_{22}H_{28}O_8$ | 62.85 (62.77) | 6.71 (6.78) | 6.00(1H, d, J=2.4), 5.97(1H, d, J=2.4), 4.64(2H, s), 4.57(2H, s), 4.35–4.15(4H, m), 2.61(2H, s), 2.0–1.4(10H, m), 1.28(6H, t, J=7.2) |
| 33 | thick syrup | | | | 11.93(1H, s), 5.98(2H, bs), 4.60(2H, s), 4.27(2H, q, J=7.0), 2.57(1H, q, J=7.0), 2.1–1.1(10H, m), 1.29(3H, t, J=7.0), 1.17(3H, d, J=7.0) |
| 34 | thick syrup | | | | 6.36(1H, d, J=2.5), 6.27(1H, d, J=2.5), 4.63(2H, s), 4.39(2H, q, J=6.0), 2.66(s) and 2.60(s)(5H), 2.1–1.2(10H, m), 1.29(3H, t, J=6.0) |
| 35 | 102–103 ether-hexane | $C_{18}H_{24}O_6$ | 65.50 (65.57) | 6.94 (7.06) | 12.0(1H, s), 5.85(1H, s), 4.63(2H, s), 4.26(2H, q, J=7.0), 2.63(2H, s), 2.09(3H, s), 2.0–1.2(13H, m) |
| 36 | thick syrup | | | | 6.60(1H, d, J=2.7), 6.35(1H, d, J=2.7), 4.61(2H, s), 4.28(2H, q, J=7.0), 2.67(2H, s), 2.1–1.2(10H, m), 1.28(3H, t, J=7.0) |
| 37 | 126–127 | | | | 6.34(1H, s), 4.75(2H, s), 4.31(2H, q, J=7.0), 2.71(2H, s), 2.0–1.3(13H, m) |
| 38 | thick syrup | | | | 6.49(1H, s), 4.75(2H, s), 4.30(2H, q, J=7.0), 2.71(2H, s), 2.2–1.2(13H, m) |
| 39 | 121–122 benzene-hexane | $C_{13}H_{14}O_6$ | 58.64 (58.52) | 5.30 (5.35) | 12.0(1H, s), 5.98(2H, s), 4.58(2H, s), 4.44(2H, t, J=6.5), 4.25(2H, q, J=7), 2.75(2H, t, J=6.5), 1.28(3H, t, J=7) |
| 40 | 71–72 ether-hexane | $C_{13}H_{14}O_5$ | 62.39 (62.25) | 5.64 (5.84) | 7.87(1H, d, J=9.0), 6.63(1H, dd, J=9.0 and 2.5), 6.41(1H, d, J=2.5), 4.66(2H, s), 4.53(2H, t, J=6.0), 4.30(2H, q, J=7.0), 2.76(2H, t, J=6.0), 1.30(3H, t, J=7.0) |
| 41 | 88–89 ether-hexane | $C_{15}H_{18}O_5$ | | | 7.83(1H, d, J=9.0), 6.58(1H, dd, J=9.0 and 2.5), 6.36(1H, d, J=2.5), 4.64(2H, s), 4.28(2H, q, J=7.0), 2.67(2H, s), 1.44(6H, s), 1.30(3H, t, J=7.0) |
| 42 | 78–79 ether-hexane | $C_{14}H_{18}O_5$ | 63.63 (63.58) | 6.10 (6.32) | 7.85(1H, d, J=9.0), 6.60(1H, dd, J=9.0 and 2.5), 6.40(1H, d, J=2.5), 4.66(2H, s), 4.58(1H, m), 4.28(2H, q, J=7.0), 2.63(2H, d, J=8.0), 1.48(3H, d, J=6.0), 1.30(3H, t, J=7.0) |
| 43 | thick syrup | | | | 7.87(1H, d, J=9.0), 7.43(5H, bs), 6.63(1H, dd, J=9.0 and 2.0), 6.45(1H, d, J=2.0), 5.45(1H, dd, J=12.0 and 4.5), 4.52(2H, s), 3.55(1H, dd, J=16.5 and 12.0), 2.70(1H, dd, J=16.5 and 4.5), 1.48(9H, s) |
| 44 | 61–62 ether-hexane | $C_{15}H_{18}O_6$ | 61.22 (61.15) | 6.17 (6.14) | 12.0(1H, s), 5.95(2H, s), 4.62(2H, s), 4.28(2H, q, J=7.0), 2.70(2H, s), 1.47(6H, s), 1.32(3H, J=7.0) |

Preparation 45

Diethyl {(3,4-dihydro-4-oxospiro[2H-1-benzopyran-2,1'-cyclohexan]-7,8-yl)dioxy}diacetate (45-1), Methyl {(7-hydroxy-3,4-dihydro-4-oxospiro[2H-1-benzopyran-2,1'-cyclohexan]-8-yl)oxy}acetate (45-2), and Methyl {(8-hydroxy-3,4-dihydro-4-oxospiro[2H-1-benzopyran-2,1'-cyclohexan]-7-yl)oxy}acetate (45-3)

A mixture of 7,8-dihydroxyspiro[2H-1-benzopyran-2,1'-cyclohexan]-4(3H)-one (prepared in Preparation 16) (4.02 g, 16.2 mmol), ethyl bromoacetate (2.98 g, 17.8 mmol), anhydrous potassium carbonate (3.35 g, 24.3 mmol), and dry acetonitrile (49 ml) is stirred overnight at room temperature. The mixture is filtered to remove the inorganic substance and the filtrate is distilled. To the residue is added diethyl ether and the mixture is extracted with 1N sodium hydroxide. Ether layer is separated, washed with water, dried, and concentrated to yield the title compound (45-1) as a syrup (2.0 g, yield 29%). The aqueous layer is made acid with dilute hydrochloric acid and extracted with diethyl ether. The ether layer is separated and extracted with aqueous sodium bicarbonate. The aqueous layer is made acidic with dilute hydrochloric acid and extracted with ether. The extract is washed with water, dried and concentrated. To the concentrate is added a mixture of diazomethane and ether to form methyl ester. The mixture is distilled to give a residue (1.8 g) containing the title compounds (45-2) and (45-3). The residue is placed onto a Lober column and eluted with a mixture of ethyl acetate and dichloromethane (1:9). From the earier fractions, the compound (45-2) is obtained as a crystalline solid (0.4 g, 7.4%, m.p.=118° 119° C.). From the succeeding fractions, the another compound (45-3) is obtained as a syrup (0.6 g, yield 11.5%).

Compound (45-1)

$^1$H-NMR (CDCl$_3$) $\delta$ppm: 7.58(1H,d,J=9), 6.47(1H,d,J=9),
4.76(2H,s), 4.73(2H,s),
4.30(2H,q,J=7), 4.23(2H,q,J=7),
2.66(2H,s), 2.2–1.2(16H,m).

Compound (45-2)

$^1$H-NMR (CDCl$_3$) $\delta$ppm: 8.53(1H,s), 7.57(1H,d,J=9),
6.56(1H,d,J=9), 4.71(2H,s),
3.83(3H,s), 2.65(2H,s),
2.15–1.2(10H,m).

Compound (45-3)

$^1$H-NMR (CDCl$_3$) $\delta$ppm: 7.40(1H,d,J=9), 6.50(1H,d,J=9),
6.27(1H,s), 4.76(2H,s),
3.82(3H,s), 2.70(2H,s),
2.1–1.2(10H,m).

Preparation 46

Ethyl 2-{(5-hydroxy-3,4-dihydro-4-oxospiro[2H-1-benzopyran-2,1'-cyclohexan]-6-yl) oxy}propionate A mixture of 5,7-dihydroxyspiro[2H-1-benzopyran-2,1'-cyclohexan]-4(3H)-one (prepared in Preparation 19) (0.248 g, 1.0 mmol), ethyl 2-bromopropionate (0.199 g, 1.1 mmol), anhydrous potassium carbonate (0.207 g, 1.5 mmol), and acetonitrile (3 ml) is stirred at room temperature for 22 hours, and the reaction mixture is concentrated. To the residue is added saturated brine and the mixture is extracted with dichloromethane. The organic layer is separated, dried, and concentrated. Purification by a silica gel column chromatography (eluent: dichloromethane) gives the title compound as an oil (0.284 g, yield 81.6%).

$^1$H-NMR (CDCl$_3$) $\delta$ppm: 11.94(1H,s), 5.93(2H,s),
4.73(1H,q, J=6.8),
4.21(2H,q,J=7), 2.63(2H,s),
1.60(3H,d,J=6.8),
2.15–1.05(10H,m),
1.26(3H,t,J=7)

Preparation 47

Ethyl 4-{(5-hydroxy-3,4-dihydro-4-oxospiro[2H-1-benzopyran-2,1'-cyclohexan]-7-yl) oxy}butyrate According to the same procedure as in Preparation 46, a mixture of 5,7-dihydroxyspiro[2H-1-benzopyran-2,1'-cyclohexan]-4(3H)-one (prepared in Preparation 19) (0.248 g, 1.0 mmol), ethyl 4-bromobutyrate (0.215 g, 1.1 mmol), anhydrous potassium carbonate (0.207 g, 1.5 mmol), and acetonitrile (3 ml) is reacted and treated. The resulting extract is concentrated and the residue is purified by a silica gel column chromatography (eluent: acetone and dichloromethane, 1:50) to obtain the title compound as an oil (0.236 g, yield 64.9%).

$^1$H-NMR (CDCl$_3$) $\delta$ppm: 12.00(1H,s), 5.96(2H,s),
4.14(2H,q, J=7),
4.02(2H,t,J=6.3), 2.63(2H,s),
2.48(2H,t,J=6.8),
2.15–1.20(12H,m),
1.24(3H,t,J=7).

Preparation 48

Ethyl 2-{(5-methoxy-3,4-dihydro-4-oxospiro[2H-1-benzopyran-2,1'-cyclopentan]-7-yl) oxy}acetate A mixture of ethyl 2-{(5-dihydroxy-3,4-dihydro-4-oxospiro [2H-1-benzopyran-2,1'-cyclopentan]-7-yl)oxy}acetate (prepared in Preparation 30) (0.99 g, 3.08 mmol), methyl iodide (0.6 g, 4.26 mmol), anhydrous potassium carbonate (0.78 g, 5.65 mmol), and dry DMF (5.6 ml) is stirred at room temperature for 4 hours under nitrogen gas. DMF is removed by distillation under reduced pressure and the residue is extracted with ether. The ether layer is washed with saturated brine, dried, and concentrated. The residue is recrystallized from ether to obtain the title compound (0.89 g, yield 94.7%, m.p.=81°-82° C.)

Elemental analysis (for $C_{18}H_{22}O_6$)
Calcd.: C, 64.66; H, 6.63
Found: C, 64.61; H, 6.50

$^1$H-NMR (CDCl$_3$) $\delta$ppm: 6.12(1H,d,J=2), 5.95(1H,d,J=2),
4.61(2H,s), 4.28(2H,q,J=7),
3.87(3H,s), 2.72(2H,s),
2.2–1.3(8H,m), 1.3(3H,t,J=7).

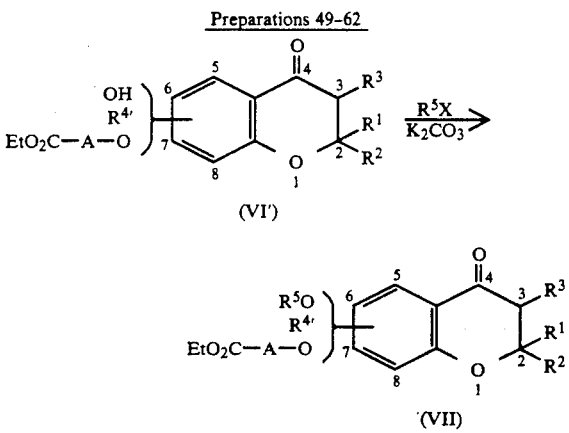

In Preparations 49 to 62, corresponding compounds (VII) were prepared according to the procedure of Preparation 48 employing the starting compound (VI') and reaction conditions given in Table 7. Purification was conducted by means of silica gel column chromatography. Physicochemical properties of each product are shwon in Table 8.

TABLE 7

| Compd. of Prep. No. | VI' material | mmol | Alkylating agent R$^5$X | potassium carbonate mmol (mmol) | DMF (ml) | Reaction conditions Temp. (°C.) | Time (hr.) | Chromato Eluent | R$^1$ | R$^2$ |
| --- | --- | --- | --- | --- | --- | --- | --- | --- | --- | --- |

TABLE 7-continued

| | | | | | | | | | | |
|---|---|---|---|---|---|---|---|---|---|---|
| 48 | 30 | 2.81 | MeI | 4.26 | 5.65 | 5.6 | 25 | 4 | — | —(CH$_2$)$_4$— |
| 49 | 31 | 1.76 | MeI | 2.29 | 3.52 | 3.5 | 25 | 3 | — | —(CH$_2$)$_5$— |
| 50 | 31 | 1.49 | EtI | 1.79 | 3.0 | 3 | 25 | 16 | — | —(CH$_2$)$_5$— |
| 51 | 31 | 1.49 | PhCH$_2$Br | 1.80 | 3.0 | 3 | 25 | 16 | ethyl acetate-dichloromethane 1:9 | —(CH$_2$)$_5$— |
| 52 | 31 | 1.49 | i-PrI | 3.0 | 4.5 | 3 | 25 60-65 | 48 8 | ethyl acetate-dichloromethane 1:9 | —(CH$_2$)$_5$— |
| 53$^{a)}$ | 31$^{b)}$ | 1.0 | CH$_2$=CHCH$_2$Br | 1.20 | 1.20 | 5 | 25 | 20 | — | —(CH$_2$)$_5$— |
| 54 | 31 | 3.0 | PhCH$_2$O(CH$_2$)$_2$OTs | 3.45 | 3$^{c)}$ | 7 | 65-70 | 20 | ethyl acetate-hexane 1:2 | —(CH$_2$)$_5$— |
| 55 | 46 | 0.82 | MeI | 1.07 | 1.64 | 3 | 25 | 23 | acetone-dichloromethane 1:9-1:20 | —(CH$_2$)$_5$— |
| 56 | 47 | 0.65 | MeI | 1.3 | 0.85 | 2 | 25 | 1.5 | acetone-dichloromethane 1:99-1:20 | —(CH$_2$)$_5$— |
| 57 | 33 | 1.12 | MeI | 1.7 | 1.7 | 3 | 25 | 4 | ethyl acetate-dichloromethane 1:9 | —(CH$_2$)$_5$— |
| 58 | 35 | 1.72 | MeI | 2.24 | 3.5 | 3.5 | 25 | 16 | ether acetate-dichloromethane 1:9 | —(CH$_2$)$_5$— |
| 59 | 39 | 2.40 | MeI | 3.12 | 4.80 | 4.8 | 25 | 5 | — | H  H |
| 60 | 44 | 3.40 | MeI | 5.11 | 6.81 | 7 | 25 | 17 | acetonitrile-dichloromethane 1:4 | Me  Me |
| 61 | 45-3 | 1.25 | MeI | 1.88 | 1.88 | 2 | 25 | 2 | ether acetate-dichloromethane 1:9 | —(CH$_2$)$_5$— |
| 62 | 45-2 | 1.25 | MeI | 1.88 | 1.88 | 2 | 25 | 2 | — | —(CH$_2$)$_5$— |

| | | | VII | | | | |
|---|---|---|---|---|---|---|---|
| Compd. of Prep. No. | R$^3$ | R$^{4'}$ | A | R$^5$ | position of —OR$^5$ | position of —O-A-COOEt | Yield (%) |
| 48 | H | H | CH$_2$ | Me | 5 | 7 | 95 |
| 49 | H | H | CH$_2$ | Me | 5 | 7 | 88 |
| 50 | H | H | CH$_2$ | Me | 5 | 7 | 98 |
| 51 | H | H | CH$_2$ | —CH$_2$Ph | 5 | 7 | 95 |
| 52 | H | H | CH$_2$ | i-Pr | 5 | 7 | 80 |
| 53$^{a)}$ | H | H | CH$_2$ | CH$_2$CH=CH$_2$ | 5 | 7 | 89 |
| 54 | H | H | CH$_2$ | (CH$_2$)$_2$OCH$_2$Ph | 5 | 7 | 70 |
| 55 | H | H | CH(CH$_3$) | Me | 5 | 7 | 85 |
| 56 | H | H | (CH$_2$)$_3$ | Me | 5 | 7 | 93 |
| 57 | Me | H | CH$_2$ | Me | 5 | 7 | 100 |
| 58 | H | 8-Me | CH$_2$ | Me | 5 | 7 | 99 |
| 59 | H | H | CH$_2$ | Me | 5 | 7 | 91 |
| 60 | H | H | CH$_2$ | Me | 5 | 7 | 76 |
| 61 | H | H | CH$_2$ | Me | 8 | 7 | 78 |
| 62 | H | H | CH$_2$ | Me | 7 | 8 | 98 |

$^{a)}$Methyl ester
$^{b)}$Methyl ester
$^{c)}$NaH

TABLE 8

| Compd. of Prep. No. | M. p. °C. (recrystallized) | Molecular formula | Elemental analysis (found) C | H | $^1$H-NMR CDCl$_3$ δ ppm (J Hz) |
|---|---|---|---|---|---|
| 48 | 81-82 ether | C$_{18}$H$_{22}$O$_6$ | 64.66 (64.61) | 6.63 (6.50) | 6.12(1H, d, J=2.0), 5.95(1H, d, J=2.0), 4.61(2H, s), 4.28(2H, q, J=7.0), 3.87(3H, s), 2.72(2H, s), 2.2-1.3(8H, m), 1.30(3H, t, J=7.0) |
| 49 | 67-68 ether-hexane | C$_{18}$H$_{24}$O$_6$ | 65.50 (65.21) | 6.94 (7.16) | 6.12(1H, d, J=2.2), 5.98(1H, d, J=2.2), 4.61(2H, s), 4.28(2H, q, J=7.0), 3.86(3H, s), 2.61(2H, s), 2.1-1.2(13H, m) |
| 50 | thick syrup | | | | 6.10(1H, d, J=2.0), 5.58(1H, d, J=2.0), 4.60(2H, s), 4.28(2H, q, J=7.0), 4.15(2H, q, J=7.0), 2.60(2H, s), 2.0-1.1(16H, m) |
| 51 | 86-87 ether-hexane | C$_{25}$H$_{28}$O$_6$ | 70.74 (70.67) | 6.65 (6.66) | 7.7-7.2(5H, m), 6.17(1H, d, J=2.0), 6.10(1H, d, J=2.0), 5.60(2H, s), 4.57(2H, s), 4.24(2H, q, J=7.0), 2.61(2H, s), 2.1-1.1(13H, m) |
| 52 | thick syrup | | | | 6.10(1H, d, J=2.0), 5.97(1H, d, J=2.0), 4.62(2H, s), 4.45(1H, m), 4.30(2H, q, J=7.0), 2.57(2H, s), 2.1-1.1(19H, m) |
| 53 | 75-76 ethyl acetate-hexane | C$_{20}$H$_{24}$O$_6$ | 66.65 (66.44) | 6.71 (6.66) | 6.17-5.98(1H, m), 6.10(1H, d, J=2.4), 5.98(1H, d, J=2.4), 5.64(1H, bd, J=17.2), 5.32(1H, bd, J=10.6), 4.63(2H, s), 4.60-4.50 (2H, m), 3.83(3H, s), 2.62(2H, s), 2.1-1.2(10H, m) |
| 54 | 83-84 ether | C$_{27}$H$_{32}$O$_7$ | 69.21 (69.26) | 6.88 (6.93) | 7.4-7.25(5H, m), 6.13(1H, d, J=2.3), 6.01(1H, d, J=2.3), 4.72(2H, s), 4.59(2H, s), 4.27(2H, q, J=7.0), 4.16(2H, bt), 3.89(2H, bt), 2.60(2H, s), 2.01-1.3(13H, m) |
| 55 | thick syrup | | | | 6.07(1H, d, J=2.2), 5.93(1H, d, J=2.2), 4.76(1H, q, J=6.5), 4.22(2H, q, J=6.8), 3.96(3H, s), 2.60(2H, s), 1.62(3H, d, J=6.5), 2.2-1.2(13H, m) |
| 56 | thick syrup | | | | 6.03(2H, s), 4.3-3.95(4H, m), 3.86(3H, s), 2.60(2H, s), 2.50(2H, t, J=6.5), |

TABLE 8-continued

| Compd. of Prep. No. | M. p. °C. (recrystallized) | Molecular formula | Elemental analysis (found) | | $^1$H-NMR CDCl$_3$ δ ppm (J Hz) |
|---|---|---|---|---|---|
| | | | C | H | |
| 57 | thick syrup | | | | 2.3–1.1(15H, m)<br>6.16(1H, d, J=2.0), 6.01(1H, d, J=2.0), 4.63(2H, s), 4.30(2H, q, J=7.0), 3.87(3H, s), 2.55(1H, q, J=7.0), 2.1–1.1(16H, m) |
| 58 | 100–101 ether-hexane | C$_{20}$H$_{26}$O$_6$ | 66.28 (66.17) | 7.23 (7.08) | 5.84(1H, s), 4.63(2H, s), 4.25(2H, q, J=7.0), 2.62(2H, s), 2.08(3H, s), 2.1–1.2(13H, m) |
| 59 | 97.5–98.5 benzene-hexane | C$_{14}$H$_{16}$O$_6$ | 59.99 (59.98) | 5.75 (5.87) | 6.13(1H, d, J=2.0), 5.97(1H, d, J=2.0), 4.60(2H, s), 4.42(2H, t, J=6.5), 4.26(2H, q, J=7), 3.87(3H, s), 2.70(2H, t, J=6.5), 1.30(3H, t, J=7) |
| 60 | 97–98 ether | C$_{16}$H$_{20}$O$_6$ | 62.33 (62.22) | 6.53 (6.50) | 6.14(1H, d, J=2.0), 5.95(1H, d, J=2.0), 4.61(2H, s), 4.28(2H, q, J=7.0), 3.88(3H, s), 2.64(2H, s), 1.40(6H, s), 1.30(3H, t, J=7.0) |
| 61 | 100–101 ether | | | | 7.55(1H, d, J=9.0), 6.45(1H, d, J=9.0), 4.76(2H, s), 3.95(3H, s), 3.80(3H, s), 2.67(2H, s), 2.15–1.2(10H, m) |
| 62 | 46–47 ether-hexane | | | | 7.60(1H, d, J=9.0), 6.57(1H, d, J=9.0), 4.68(2H, s), 3.91(3H, s), 3.82(3H, s), 2.67(2H, s), 2.1–1.2(10H, m) |

Preparation 63

Ethyl 4-{(5-(2-hydroxy)ethyl-3,4-dihydro-4-oxospiro[2H-1-benzopyran-2,1'-cyclohexan ]-7-yl)oxy}acetate A solution of ethyl 4-{(5-(2-benzyloxy)ethyl-3,4-dihydro-4-oxospiro[2H-1-benzopyran-2,1'-cyclohexan]-7-yl)-oxy}acetate(prepared in Preparation 54) (0.347 g, 0.74 mmol) in a mixture of ethyl acetate and ethanol (1:3) (7 ml) is hydrogenated over 10% Palladium on activated carbon at room temperature until theoretical amount of hydrogen is consumed. The catalyst is removed by filtration and the filtrate is concentrated. The residue is placed on a silica gel column and eluted with a mixture of ethyl acetate and dichloromethane (1:9) to yield the title compound as a crude crystalline solid (0.235 g, 84%). Recrystallization from diethyl ether gives a product having a melting point of 104°–105° C.

Elemental analysis (for C$_{20}$H$_{26}$O$_7$)
Calcd.: C, 63.48; H, 6.92
Found: C, 63.37; H, 6.95
$^1$H-NMR (CDCl$_3$) δppm: 6.14(1H,d,J=2.3), 6.05(1H,d,J=2.3), 4.62(2H,s), 4.29(2H,q,J=7), 4.2–3.8(4H,m), 2.63(2H,s), 2.1–1.2(10H,m), 1.30(3H,t,J=7).

Preparation 64

Ethyl 2-{(6-chloro-3,4-dihydro-4-oxospiro [2H-1-benzopyran-2,1'-cyclohexan]-7-yl)oxy}acetate Ethyl 2-{(3,4-dihydro-4-oxospiro[2H-1-benzopyran-2,1'-cyclohexan]7-yl)oxy}acetate prepared in Preparation 28) (0.72 g, 2.26 mmol) is dissolved in dry dichloromethane (7.2 ml). To the solution is added dropwise 1M sulfuryl chloride solution in dichloromethane (2.3 ml, 2.3 mmol) at −40° C. with stirring. After 2 hours stirring at −40° to −10° C., the solvent is removed by distillation. The residue is dissolved in dichloromethane, and the solution is washed with water, dried, and concentrated. The residue is applied to a Lober column and eluted with a mixture of ethyl acetate and hexane (1:2). The resulting crude product is recrystallized from a mixture of diethyl ether and hexane to yield the title compound (0.6 g, yield 75%, m.p.=116°–117° C.).

Elemental analysis (for C$_{18}$H$_{21}$ClO$_5$)
Calcd.: C, 61.28; H, 6.00; Cl, 10.05
Found: C, 61.30; H, 6.13; Cl, 10.13
$^1$H-NMR (CDCl$_3$) δppm: 7.86(1H,s), 6.36(1H,s), 4.72(2H,s), 4.27(2H,q,J=7), 2.63(2H,s), 2.1–1.1(13H,m).

Preparation 65

Ethyl 2-{(6,8-dichloro-5-methoxy-3,4-dihydro-4-oxospiro[2H-1-benzopyran-2,1'-cyclohe xan]-7-yl)oxy}acetate (65-1), Ethyl 2-{(6-chloro-5-methoxy-3,4-dihydro-4-oxospiro[2H-1-benzopyran-2,1 '-cyclohexan]-7-yl)oxy}acetate (65-2), and Ethyl 2-{(8-chloro-5-methoxy-3,4-dihydro -4-oxospiro[2H-1-benzopyran-2,1'-cyclohexan]-7-yl)oxy}acetate (65-3)

Ethyl 2-{(5-methoxy-3,4-dihydro-4-oxospiro [2H-1-benzopyran-2,1'-cyclohexan]-7-yl)oxy}acetate (prepared in Preparation 49) (0.64 g, 1.83 mmol) is dissolved in dry dichloromethane (11 ml). To the solution is added dropwise 1M sulfuryl chloride solution in dichloromethane (2.0 ml) at −30° to −25° C. with stirring. After 15 minutes stirring at the same temperature, the solvent is removed by distillation. The residue is applied to a Lober column and eluted with a mixture of ethyl acetate and dichloromethane (1:9). From the earlier fractions, the compound (65-1) (50 mg, yield 6.5%) is obtained. Recrystallization from hexane gives a compound having a melting point of 87°–88° C. From the succeeding fractions, the compound (65-2) (0.233 g, yield 33.1%) is obtained. Recrystallization from a mixture of diethyl ether and hexane gives the compound having a melting point of 104°–105° C. From the last fraction, the compound (65-3) (0.394 g, yield 56%) is obtained. Recrystallization from a mixture of benzene and hexane gives the compound having a melting point of 129°–130° C.

Compound (65-1)

Elemental analysis (for C$_{19}$H$_{22}$Cl$_2$O$_6$)
Calcd.: C, 54.69; H, 5.31; Cl, 16.99
Found: C, 54.77; H, 5.42; Cl, 17.10
$^1$H-NMR (CDCl$_3$) δppm: 4.70(2H,s), 4.30(2H,q,J=7),
3.88(3H,s), 2.69(2H,s),
2.2–1.25(13H,m).

Compound (65-2)

Elemental analysis (for C$_{19}$H$_{23}$ClO$_6$)
Calcd.: C, 59.61; H, 6.05; Cl, 9.26
Found: C, 59.63; H, 5.93; Cl, 9.19
$^1$H-NMR (CDCl$_3$) δppm: 6.20(1H,s), 4.72(2H,s), 4.28(2H,q,J=7), 3.88(3H,s),
2.62(2H,s), 2.1–1.2(13H,m).

Compound (65-3)

Elemental analysis (for C$_{19}$H$_{23}$ClO$_6$)
Calcd.: C, 59.61; H, 6.05; Cl, 9.26

Found: C, 59.59; H, 6.02; Cl, 9.05
¹H-NMR (CDCl₃) δppm: 6.02(1H,s), 4.76(2H,s),
4.27(2H,q,J=7), 3.85(3H,s),
2.62(2H,s), 2.2–1.2(13H,m).

Preparation 66

Ethyl 2-{(8-chloro-5-hydroxy-3,4-dihydro-4-oxospiro[2H-1-benzopyran-2,1'-cyclohexan]-7-yl)oxy}acetate Ethyl 2-{(8-chloro-5-methoxy-3,4-dihydro-4-oxospiro[2H-1-benzopyran-2,1'-cyclohexan]-7-yl)oxy}acetate (65-3, prepared in Preparation 65) (0.575 g, 1.50 mmol) is dissolved in dry dichloromethane (3 ml). To the solution is added dropwise a 2M boron trichloride solution in dichloromethane (1.5 ml, 3.0 mmol) at −75° to −70° C. After stirring at −70° to −50° C. for 1.5 hours, ice-cold water is added thereto and the mixture is extracted with dichloromethane. Organic layer is separated, washed with aqueous sodium bicarbonate, dried, and concentrated. The residue is applied to a silica gel column and eluted with a mixture of acetonitrile and dichloromethane (1:9) to yield the title compound as a crystalline solid (0.428 g, yield 77.4%). Recrystallization from diethyl ether gives a product having a melting point of 110°–111° C.

Elemental analysis (for C₁₈H₂₀ClO₆)
Calcd.: C, 58.62; H, 5.74; Cl, 9.61
Found: C, 58.60; H, 5.69; Cl, 9.73
¹H-NMR (CDCl₃) δppm: 10.95(1H,s), 5.94(1H,s),
4.71(2H,s), 4.28(2H,q,J=7),
2.69(2H,s), 2.2–1.2(13H,m).

Preparation 67

Ethyl 2-{(6-chloro-5-hydroxy-3,4-dihydro-4-oxospiro[2H-1benzopyran-2,1'-cyclohexan]-7-yl)oxy}acetate According to the procedure of Preparation 66 employing ethyl 2-{(6-chloro-5-methoxy-3,4-dihydro-4-oxospiro[2H-1-benzopyran-2,1'-cyclohexan]-7-yl)oxy}acetate (65-2, prepared in Preparation 65) (0.65 g, 1.7 mmol) and 2M boron trichloride solution in dichloromethane (1.7 ml, 3.4 mmol), the title compound is prepared as a crystalline solid (0.62 g, yield 94%). Recrystallization from cyclohexane gives a product having a melting point of 103°–104° C.

Elementary analysis (for C₁₈H₂₀ClO₆)
Calcd.: C, 58.62; H, 5.74; Cl, 9.61
Found: C, 58.53; H, 5.67; Cl, 9.78
¹H-NMR (CDCl₃) δppm: 12.4(1H,s), 5.94(1H,s),
4.72(2H,s), 4.28(2H,q,J=7),
2.69(2H,s), 2.2–1.2(13H,m).

Preparation 68

Ethyl 2-{(6,8-dichloro-5-hydroxy-3,4-dihydro-4-oxospiro[2H-1-benzopyran-2,1'-cyclohexan]-7-yl)oxy}acetate According to the procedure of Preparation 66 employing ethyl 2-{(6,8-dichloro-5-methoxy-3,4-dihydro-4-oxospiro[2H-1-benzopyran-2,1'-cyclohexan]-7-yl)oxy}acetate (65-1, prepared in Preparation 65) (0.635 g, 1.52 mmol) and 2M boron trichloride solution in dichloromethane (1.7 ml, 3.4 mmol), the title compound is prepared as a crystalline solid (0.60 g, yield 98%). Recrystallizaton from a mixture of diethyl ether and hexane gives a product having a melting point of 134°–135° C.

Elemental analysis (for C₁₈H₂₀Cl₂O₆)
Calcd.: C, 53.61; H, 5.00; Cl, 17.59
Found: C, 53.34; H, 4.98; Cl, 17.42
¹H-NMR (CDCl₃) δppm: 12.35(1H,s), 4.70(2H,s),
4.29(2H,q,J=7), 2.74(2H,s),
2.2–1.2(13H,m).

Preparation 69

Ethyl 2-{(5-methoxy-8-nitro-3,4-dihydro-4-oxospiro[2H-1-benzopyran-2,1'-cyclohexan]-7-yl)oxy}acetate Ethyl 2-{(5-methoxy-3,4-dihydro-4-oxospiro[2H-1-benzopyran-2,1'-cyclohexan]-7-yl) oxy}acetate prepared in Preparation 49) (1.3 g, 3.92 mmol) is added by portions to fuming nitric acid (d=1.50, 10 ml) at −60° C. with stirring. After one hour stirring at −60° to −40° C., the reaction mixture is poured into ice-cold water. The mixture is extracted with diethyl ether. The ether layer is separated, washed with water and then aqueous sodium bicarbonate, dried and concentrated. The residue is washed with diethyl ether. Recrystallization from a mixture of ethyl acetate and hexane gives the title compounds as a crystalline solid (1.05 g, yield 74.2%, m.p.=142°–143° C.).

Elemental analysis (for C₁₉H₂₃NO₈)
Calcd.: C, 58.00; H, 5.89; N, 3.56
Found: C, 57.93; H, 5.89; N, 3.60
¹H-NMR (CDCl₃) δppm: 5.99(1H,s), 4.74(2H,s),
4.26(2H,q,J=7), 3.89(3H,s),
2.65(2H,s), 2.1–1.2(13H,m).

Preparation 70

Ethyl 2-{(5-methoxy-8-chlorosulfonyl-3,4-dihydro-4-oxospiro[2H-1-benzopyran-2,1'-cyclohexan]-7-yl)oxy}acetate To a solution of ethyl 2-{(5-methoxy-3,4-dihydro-4-oxospiro[2H-1-benzopyran-2,1'-cyclohexan]-7-yl)oxy}acetate (prepared in Preparation 49) (0.80 g, 2.29 mmol) in dry dichloromethane (6 ml) is added chlorosulfonic acid (1.6 g, 13.7 mmol) with stirring while cooling on ice. After 1.5 hours reaction at room temperature, chlorosulfonic acid (0.54 g, 4.64 mmol) is added thereto and the reaction is continued at room temperature for additional 0.5 hours. To the mixture is added thionyl chloride (1.09 g, 9.16 mmol) and the mixture is heated to reflux for 1.5 hours. The reaction mixture is poured into ice-cold water, and the solution is stirred for 10 minutes, and extracted with ethyl acetate. The ethyl acetate layer is separated and washed with saturated brine, dried, and concentrated to yield the title compound as a crystalline solid (0.99 g, yield 96%, m.p.=74°–78° C.). The product is employed to the next step without purification.

Preparation 71

Ethyl 2-{(5-methoxy-8-sulfamoyl-3,4-dihydro-4-oxospiro[2H-1-benzopyran-2,1'-cyclohexan]-7-yl)oxy}acetate A solution of ethyl 2-{(5-methoxy-8-chlorosulfonyl-3,4-dihydro-4-oxospiro[2H-1-benzopyran-2,1'-cyclohexan]-7-yl)oxy}acetate (prepared in Preparation 70) (0.32 g, 0.74 mmol) in dichloromethane (4 ml) is added dropwise to a solution of liquid ammonia (2 ml, 80 mmol) and triethylamine (0.1 ml, 0.7 mmol) in dichloromethane (4 ml) at −25° to −20° C. After stirring at the same temperature for 30 minutes, the solvent is removed by distillation. The residue is placed on a silica gel column and eluted with a mixture of acetone and dichloromethane (1:1) to yield the title compound as a crystalline solid (0.173 g, yield 56.5%). Recrystallization from a mixture of ethyl acetate and ether gives a product having a melting point of 188°-190° C.

Elemental analysis (for $C_{19}H_{25}NO_8S$)
Calcd C, 53.39; H, 5.89; N, 3.28; S, 7.50
Found: C, 53.19; H, 5.90; N, 3.20; S, 7.56
$^1$H-NMR (CDCl$_3$) δppm: 5.96(1H,s), 5.88(2H,s), 4.78(2H,s), 4.34(2H,q,J=7),
3.94(3H,s), 2.66(2H,s),
2.15-1.2(10H,m),
1.34(3H,t,J=7).

Preparation 72

Ethyl 2-{(5-methoxy-8-N-methylsulfamoyl-3,4-dihydro-4-oxospiro[2H-1-benzopyran-2,1'-cyclohexan]-7-yl) oxy}acetate To a solution of ethyl 2-{(5-methoxy-8-chlorosulfonyl-3,4-dihydro-4-oxospiro[2H-1-benzopyran-2,1'-cyclohexan]-7-yl)oxy}acetate (prepared in Preparation 70) (0.30 g, 0.70 mmol), triethylamine (0.87 ml, 6.2 mmol) in acetone (6.7 ml) is added dropwise a 30% methylamine solution in ethanol (0.181 g, 1.5 mmol) at −30° to −20° C. over 10 minutes. After 30 minutes stirring at the same temperature, the solvent is removed by distillation. The residue is dissolved in ethyl acetate. The solution is washed with dilute hydrochloric acid and then saturated brine, dried, and concentrated. The residue is placed on a silica gel column and eluted with a mixture of ethyl acetate and dichloromethane (1:1) to yield the title compound as a crystalline solid (0.244 g, yield 82.4%). Recrystallization from ethyl acetate gives a product having a melting point of 177°-178° C.

Elemental analysis (for $C_{20}H_{27}NO_8S$)
Calcd.: C, 54.41; H, 6.16; N, 3.17; S, 7.26
Found: C, 54.17; H, 6.06; N, 3.19; S, 7.12
$^1$H-NMR (CDCl$_3$) δppm: 6.17(1H,q,J=5.2), 5.95(1H,s),
4.76(2H,s), 4.34(2H,q,J=7.2),
3.94(3H,s), 2.70(3H,d,J=5.2),
2.66(2H,s), 2.15-1.2(10H,m),
1.35(3H,t,J=7.2).

Preparation 73

Ethyl 2-{(5-methoxy-8-N,N-dimethylsulfamoyl-3,4-dihydro-4-oxospiro[2H-1-benzopyran-2,1'-cyclohexan]-7-yl) oxy}acetate A solution of ethyl 2-{(5-methoxy-8-chlorosulfonyl-3,4-dihydro-4-oxospiro[2H-1-benzopyran-2,1'-cyclohexan]-7-yl)oxy}acetate (prepared in Preparation 70) (0.35 g, 0.81 mmol) in acetone (7 ml) is added dropwise to a mixture of 50% aqueous dimethylamine (0.085 g, 0.94 mmol), acetone (2 ml), and triethylamine (0.096 g, 0.95 mmol) at −30° C. The mixture is stirred at −30° to −20° C. for 20 minutes. The reaction mixture is treated in the same manner as in Preparation 72. The resulting residue is chromatographed (eluent: acetone and dichloromethane, 1:1) to yield the title compound as a crystalline solid (0.30 g, yield 84.1%). Recrystallization from diethyl ether gives a product having a melting point of 237°-238° C.

Elemental analysis (for $C_{21}H_{29}NO_8S$)
Calcd.: C, 55.37; H, 6.42; N, 3.07; S, 7.04
Found: C, 55.20; H, 6.30; N, 3.06; S, 6.74
$^1$H-NMR (CDCl$_3$) δppm: 5.93(1H,s), 4.78(2H,s),
4.28(2H,q,J=7.2), 3.90(3H,s),
2.92(6H,s), 2.66(2H,s),
2.1-1.2(10H,m),
1.3(3H,t,J=7.2).

Preparation 74

Ethyl 2-{(7-methoxy-3,4-dihydro-4-oxospiro[2H-1-benzopyran-2,1'-cyclohexan]-5-yl) oxy}acetate To a solution of 5,7-dimethoxy-spiro[2H-1-benzopyran-2,1'-cyclohexan]-4(3H)-one (prepared in Preparation 8) (0.70 g, 2.54 mmol) in dry dichloromethane (5 ml) is added dropwise 2M boron trichloride solution in dichloromethane (3 ml, 6 mmol) at −35° C. After one hour stirring at −30° to 0° C., ice-cold water is added to the mixture and the mixture is extracted with dichloromethane. The dichloromethane layer is washed with water, dried, and concentrated to yield 5-hydroxy-7-methoxyspiro[2H-1-benzopyran-2,1'-cyclohexan]-4(3H)-one as a crude crystalline solid (0.66 g, 99.5%). Recrystallization from hexane gives a product having a melting point of 69°-70° C.

A mixture of the above compound (0.71 g, 2.71 mmol), ethyl bromoacetate (0.542 g, 3.69 mmol), sodium iodide (0.02 g, 0.13 mmol), anhydrous potassium carbonate (0.56 g, 4.06 mmol) and DMF (9 ml) is stirred three overnights at room temperature. The mixture is treated in the same manner as in Preparation 27 to yield the title compound as a thick syrup (0.80 g, yield 85%).

$^1$H-NMR (CDCl$_3$) δppm: 6.10(1H,d,J=2), 5.89(1H,d,J=2),
4.64(2H,s), 4.25(2H,q,J=7),
3.78(3H,s), 2.61(2H,s),
2.1-1.2(13H,m).

Preparation 75

(4'-Acetylamino-2',6'-dimethoxyphenyl)ethanone (75-1), (4'-acetylamino-2'-hydroxy-6'-methoxyphenyl)ethanone (75-2), and (2'-acetylamino-4',6'-dimethoxyphenyl)ethanone (75-3)

To a solution of acetyl chloride (9.42 g, 0.12 mol) in dry dichloromethane (200 ml) is added anhydrous aluminium chloride (26.68 g, 0.2 mol) at room temperature with stirring and reacted for 0.5 hours, which is followed by the addition of N-3',5'-dimethoxyphenylacetamide (18.2 g, 0.093 mol) keeping the temperature below 10° C. After 1.5 hours reaction at room temperature, the mixture is diluted with dichloromethane, poured into 10% ice-cooled hydrochloric acid, and extracted with dichloromethane. The dichloromethane layer is washed with water, dried, and the solvent is removed by distillation. The residue is placed on a silica gel column and eluted with a mixture of ethylacetate and dichloromethane (1:1). From the earlier fraction, the title compound (75-3) (4.2 g, 19%) is obtained. From the succeeding fractions, the title compound (75-2) (2.23 g, 11%) and (75-1) (12.3 g, 50%) are obtained, successively. Each compound is employed to the next step without purification.

Compound (75-1); m.p.=194°-195° C.
Elemental analysis (for $C_{12}H_{15}NO_4$)
Calcd.: C, 60.76; H, 6.37; N, 5.90
Found: C, 60.41; H, 6.24; N, 5.88
$^1$H-NMR (CDCl$_3$) δppm: 8.15(1H,b), 6.80(2H,s),
3.70(6H,s), 2.45(3H,s),
2.12(3H,s).

Compound (75-2); m.p.=196°-197° C.
Elemental analysis (for $C_{11}H_{13}NO_4$)
Calcd.: C, 59.19; H, 5.87; N, 6.28
Found: C, 59.00; H, 5.78; N, 6.13
$^1$H-NMR (CDCl$_3$) δppm: 13.57(1H,s), 7.50(1H,b),
7.10(1H,d,J=1.5),
6.31(1H,d,J=1.5), 3.85(3H,s), 2.60(3H,s), 2.17(3H,s).
Compound (75-3); m.p.=105°-106° C.
Elemental analysis (for C$_{12}$H$_{15}$NO$_4$)
Calcd.: C, 60.76; H, 6.37; N, 5.90
Found: C, 60.74; H, 6.30; N, 5.76
$^1$H-NMR (CDCl$_3$) δppm: 11.70(1H,b), 8.00(1H,d,J=3),
6.18(1H,d,J=3),
3.81(6H,s), 2.56(3H,s),
2.18(3H,s).

Preparation 76

(4'-Amino-2',6'-dimethoxyphenyl)ethanone

A mixture of (4'-acetylamino-2',6'-dimethoxyphenyl)ethanone (compound 75-1) (7.11 g, 0.03 mol) and 10% potassium hydroxide solution in ethanol is heated to reflux for 3 hours. The solvent is distilled from the reaction mixture under reduced pressure. The residue is dissolved in dichloromethane, and the solution is washed with water, dried, and concentrated. The residue is placed on a silica gel column and eluted with a mixture of ethylacetate and dichloromethane (1:1) to yield the title compound as a crystalline solid (5.54 g, 95%, m.p.=154°-155° C.).

Elemental analysis (for C$_{10}$H$_{13}$NO$_3$)
Calcd.: C, 61.53; H, 6.71; N, 7.18
Found: C, 61.50; H, 6.69; N, 7.20
$^1$H-NMR (CDCl$_3$) δppm: 5.86(2H,s), 3.76(2H,b), 3.76(6H,s), 2.43(3H,s).

Preparation 77

(4',6'-Dimethoxy-2'-mercaptophenyl)ethanone

A solution of (2'-hydroxy-4',6'-dimethoxyphenyl)ethanone (Table 1, literature No. d) (8 g, 40.8 mmol) in dry DMF (31 ml) is added dropwise to a suspension of 60% sodium hydride (1.71 g, 42.8 mmol) in DMF (10 ml) under ice-cooling under nitrogen atmosphere. After 5 minutes stirring at room temperature, N,N-dimethylthiocarbamoyl chloride (6.55 g, 53 mmol) is added to the mixture. The mixture is heated at 55° to 60° C. for one hour with stirring. To the reaction mixture is added ice-cooled saturated aqueous ammonium chloride solution. The mixture is extracted with a mixture of ethyl acetate and dichloromethane (2:1). The extract is washed with saturated brine, dried, and the solvent is removed by distillation. The residue is treated with diethyl ether, and the mixture is filtered to obtain a crystalline solid (4.84 g). The mother liquor is applied to a silica gel column. The column is developed with a mixture of ethyl acetate and dichloromethane (1:9) to obtain an additional crystalline solid (1.43 g). The overall yield of O-(2-acetyl-3,5-dimethoxyphenyl)-N,N-dimethylthiocarbamate is 6.25 g (54%).

This crystal (3.0 g, 11.2 mmol) is dissolved in diphenyl ether (30 ml) and the solution is heated at 220° to 230° C. for one hour with stirring under nitrogen gas. Diphenyl ether is removed under reduced pressure. The residue is placed on a silica gel column and eluted with a mixture of ethyl acetate and dichloromethane (1:9) to obtain S-(2-acetyl-3,5-dimethoxyphenyl)-N,N-dimethylthiocarbamate as a thick syrup (1.0 g, yield 33%).

A solution of the thick syrup (1.0 g, 3.75 mmol) and 2N sodium hydroxide (2.3 ml) in methanol (10 ml) is heated to reflux for one hour under nitrogen gas. After the mixture is made acid with dilute hydrochloric acid, methanol is removed under reduced pressure and the residue is extracted with diethyl ether. The extract is washed with saturated brine, dried, and the solvent is removed by distillation. The residue is placed on a silica gel column and eluted with a mixture of ethyl acetate and dichloromethane (1:9). The eluate is again applied to a silica gel column and eluted with a mixture of ethyl acetate and benzene (1:9) to obtain the title compound as a crystalline solid (0.56 g, yield 76%, m.p.=57°-59° C.).

$^1$H-NMR (CDCl$_3$) δppm: 6.42(1H,d,J=2.2), 6.26(1H,d,J=2.2), 4.12(1H,s),
3.85(3H,s), 3.82(3H,s),
2.54(3H,s).

Preparation 78

5,7-Dimethoxyspiro[2H-1-benzothiin-2,1'-cyclohexan]-4(3H)-one

A solution of (4',6'-dimethoxy-2'-mercaptophenyl)ethanone (prepared in Preparation 77) (0.53 g, 2.5 mmol) and cyclohexanonepyrrolidine enamine (0.57 g, 3.73 mmol) in dry methanol (8 ml) is heated to reflux for 3 hours under nitrogen gas. The solvent is removed by distillation and the residue is dissolved in diethyl ether. The solution is washed with dilute hydrochloric acid and then saturated brine, dried, and the solvent is removed. The residue is placed on a silica gel column and eluted with a mixture of ethyl acetate and dichloromethane (1:9). The starting material (0.142 g, 26%) and the title compound (crystalline solid, 0.526 g, 71.9%) are obtained, successively. Recrystallization from diethyl ether gives the title compound having a melting point of 104°-105° C.

Elemental analysis (for C$_{16}$H$_{20}$O$_3$S)
Calcd.: C, 65.72; H, 6.89; S, 10.96
Found: C, 65.73; H, 6.90; S, 10.67
$^1$H-NMR (CDCl$_3$) δppm: 6.35(1H,d,J=2.2), 6.20(1H,d,J=2.2), 3.86(3H,s),
3.82(3H,s), 2.88(2H,s),
1.95–1.20(10H,m).

Preparation 79

5,7-Dihydroxyspiro[2H-1-benzothiin-2,1'-cyclohexan]-4(3H)-one

A mixture of 5,7-Dimethoxyspiro[2H-1-benzothiin-2,1'-cyclohexan]-4(3H)-one (prepared in Preparation 78) (0.526 g, 1.80 mmol) and pyridine hydrochloride (4 g, 34.6 mmol) is heated at 205°-210° C. for 50 minutes with stirring under nitrogen gas. After cooling, dilute HCl is added to the mixture. The mixture is extracted with diethyl ether. The extract is washed with saturated brine, dried, and the solvent is removed. The residue is placed on a silica gel column and eluted with a mixture of ethyl acetate and dichloromethane (1:9) to obtain the title compound as a crystalline solid (0.459 g, 96%). Recrystallization from diethyl ether gives a product having a melting point of 160°-162° C.

$^1$H-NMR (CDCl$_3$) δppm: 13.04(1H,s), 7.5(1H,b), 6.27(1H,d,J=2.2),
6.08(1H,d,J=2.2),
2.87(2H,s), 2.0–1.1(10H,m).

Preparation 80

5,7-Dimethoxyspiro[1,2,3,4-tetrahydroquinoline-2,1'-cyclohexan]-4-one

A mixture of (2'-acetylamino-4',6'-dimethoxyphenyl)ethanone (compound 75-3, prepared in Preparation 75) (0.237 g, 1.0 mmol), potassium hydroxide (0.2 g, 3.57 mmol), water (0.2 ml), and ethanol (2 ml) is heated to reflux for one hour. The solvent is distilled under reduced pressure, and the residue is extracted with dichloromethane. The extract is washed with water, dried, and the solvent is removed to yield a crystalline residue. Recrystallization from ethyl acetate gives (2'-amino-4',6'-dimethoxyphenyl)ethanone as a crystalline solid (0.114 g, 58%, m.p.=104°-105° C.).

A solution of (2'-amino-4',6'-dimethoxyphenyl) ethanone (3.25 g, 16.7 mmol) in absolute methanol (300 ml) is added cyclohexanonepyrrolidine enamine (5.54 g, 36.2 mmol) and pyrrolidine (2.37 g, 33.4 mmol). The mixture is heated to reflux for 65 hours under argon gas, then the solvent is removed under reduced pressure. Ethyl acetate and diethyl ether are added to the residue and the mixture is filtered to remove insoluble matter including starting materials (0.87 g). The ethyl acetate layer is separated, washed, dried and the solvent is removed by distillation. The residue is placed on a silica gel column and eluted with a mixture of acetone and dichloromethane (1:5) to obtain the title compound as a crystalline solid (0.88 g, 20%). Recrystallization from a mixture of dichloromethane and diethyl ether gives a product having a melting point of 168°-169° C.

Elemental analysis (for $C_{16}H_{21}NO_3$)
Calcd : C, 69.80; H, 7.69; N, 5.09
Found: C, 69.65; H, 7.57; N, 4.98
$^1$H-NMR (CDCl$_3$) δppm: 5.77(1H,d,J=2.2), 5.70(1H,d,J=2.2), 4.49(1H,b),
3.84(3H,s), 3.79(3H,s),
2.57(2H,s), 2.2-1.2(10H,m).

Preparation 81

5,7-Dihydroxyspiro[1,2,3,4-tetrahydroquinoline-2,1'-cyclohexan]-4-one

A mixture of 5,7-dimethoxyspiro[1,2,3,4-tetrahydroquinoline-2,1'-cyclohexan]-4-one (prepared in Preparation 80) (0.422 g, 1.53 mmol) and pyridine hydrochloride (1.2 g, 10.4 mmol) is heated at 190° C. for one hour with stirring under nitrogen gas. After cooling, dilute hydrochloric acid is added to the mixture and the mixture is extracted with ethyl acetate. The extract is washed with saturated brine, dried, and the solvent is removed by distillation. The residue is placed on a silica gel column and eluted with a mixture of ethyl acetate and dichloromethane (1:3). From the earlier fractions, 5-hydroxy-7-methoxyspiro[1,2,3,4-tetrahydroquinoline-2,1'-cyclohexan]-4-one is obtained as a crystalline solid (0.098 g, 25%). From the succeeding fractions, the title compound is obtained as a crystalline solid (0.26 g, 68%). Recrystallization from diethyl ether gives a product having a melting point of 132°-133° C.

Elemental analysis (for $C_{14}H_{17}NO_3 \cdot \frac{1}{4}H_2O$)
Calcd.: C, 66.65; H, 7.46; N, 5.18
Found: C, 66.47; H, 7.13; N, 5.25
$^1$H-NMR (CDCl$_3$) δppm: 12.5(1H,s), 5.67(1H,d,J=2.2),
5.60(1H,b), 5.56(1H,d,J=2.2),
4.45(1H,b), 2.60(2H,s),
1.8-1.2(10H,m).

Example 1

{(3,4-Dihydro-4-oxospiro[2H-1-benzopyran-2,1'-cyclohexan]-6-yl)oxy}acetic acid

A mixture of ethyl (2-{(3,4-dihydro-4-oxospiro [2H-1-benzopyran-2,1'-cyclohexan]-6-yl)oxy}acetate (prepared in Preparation 27) (0.5 g, 1.57 mmol) and 1N sodium hydroxide (1.9 ml, 1.9 mmol), and ethanol (5 ml) is stirred at room temperature for one hour. The mixture is made acid with 1N HCl, filtered, and washed with small amount of water to separate crystalline precipitates. Recrystallization from a mixture of diethyl ether and hexane gives the title compound as a crystalline solid (0.39 g, 85.6%, m.p.=148°-149° C.).

Elemental analysis (for $C_{16}H_{18}O_5$)
Calcd.: C, 66.19; H, 6.25
Found: C, 66.03; H, 6.35
$^1$H-NMR (d$_6$-DMSO) δppm: 7.23(1H,dd,J=9,2), 7.16(1H,d,J=2), 6.99(1H,d,J=9),
4.67(2H,s), 2.74(2H,s),
2.1-1.1(10H,m).

Example 2-47

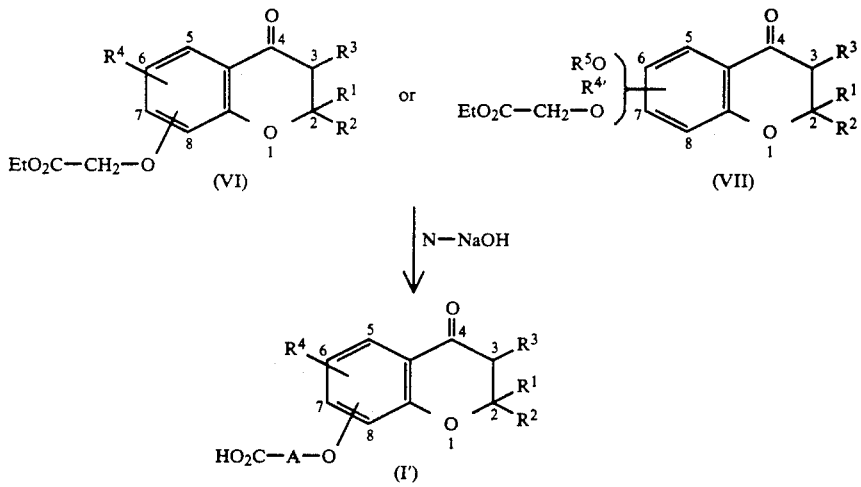

In Examples 2 to 47, corresponding compounds (I') were prepared according to the procedure of Example 1 employing the starting materials (VI or VII) and reaction conditions given in Table 9. Physicochemical properties of each product are shown in Table 10.

TABLE 9

| Compound of Example | VI, VII Prep. | N—NaOH | EtOH | Reaction condition Temp. | Time | I' |
|---|---|---|---|---|---|---|

TABLE 9-continued

| No. | No. | mmol | (ml) | (ml) | (°C.) | (hr.) | R¹ | R² | R³ | R⁴ |
|---|---|---|---|---|---|---|---|---|---|---|
| 1 | 27 | 1.57 | 1.9 | 5 | 25 | 1 | —(CH₂)₅— | | H | H |
| 2 | 28 | 1.87 | 4.5 | 4.5 | 25 | 1 | —(CH₂)₅— | | H | H |
| 3 | 29 | 1.3 | 2.9 | 4 | 25 | 0.5 | Me | Ph | H | 5-OH |
| 4 | 30 | 1.87 | 4.5 | 4.5 | 25 | 1 | —(CH₂)₄— | | H | 5-OH |
| 5 | 31 | 1.6 | 3.6 | 5 | 25 | 0.5 | —(CH₂)₅— | | H | 5-OH |
| 6 | 32 | 3.67 | 8.8 | 16 | 25 | 0.7 | —(CH₂)₅— | | H | 5-OCH₂COOH |
| 7 | 34 | 1.87 | 4.5 | 4.5 | 25 | 1 | —(CH₂)₅— | | H | 5-Me |
| 8 | 35 | 1.87 | 4.5 | 4.5 | 25 | 1 | —(CH₂)₅— | | H | 5-OH 8-Me |
| 9 | 36 | 2.86 | 3.4 | 10 | 25 | 1 | —(CH₂)₅— | | H | 5-Cl |
| 10 | 37 | 1.11 | 1.3 | 8 | 25 | 1 | —(CH₂)₅— | | H | 5-Cl 6-Cl |
| 11 | 38 | 0.77 | 1.0 | 3 | 25 | 1 | —(CH₂)₅— | | H | 5-Cl 8-Cl |
| 12 | 39 | 1.13 | 2.5 | 10 | 25 | 1 | H | H | H | 5-OH |
| 13 | 40 | 5.68 | 6.8 | — | 25 | 1 | H | H | H | H |
| 14 | 41 | 6.0 | 7.2 | — | 25 | 1 | Me | Me | H | H |
| 15 | 42 | 6.0 | 7.2 | — | 25 | 1 | H | Me | H | H |
| 16 | 43 | 2.15 | 7.6 (trifluoro acetic acid) | — | 25 | 1 | H | Ph | H | H |
| 17 | 44 | 6.0 | 13.2 | — | 25 | 1 | Me | Me | H | 5-OH |
| 18 | 45-1 | 4.5 | 9.9 | 19 | 25 | 1 | —(CH₂)₅— | | H | 8-OCH₂COOH |
| 19 | 45-2 | 0.30 | 0.4 | 2 | 25 | 1 | —(CH₂)₅— | | H | 7-OH |
| 20 | 48 | 2.66 | 3.2 | 9 | 25 | 1 | —(CH₂)₄— | | H | 5-OMe |
| 21 | 49 | 1.40 | 3.0 | 4 | 25 | 20 | —(CH₂)₅— | | H | 5-OMe |
| 22 | 50 | 2.66 | 3.2 | 9 | 25 | 1 | —(CH₂)₅— | | H | 5-OEt |
| 23 | 51 | 2.66 | 3.2 | 9 | 25 | 1 | —(CH₂)₅— | | H | 5-OCH₂Ph |
| 24 | 52 | 2.66 | 3.2 | 9 | 25 | 1 | —(CH₂)₅— | | H | 5-OPr-i |
| 25 | 53 | 0.64 | 0.77 | 3 | 25 | 1 | —(CH₂)₅— | | H | 5-OCH₂CH═CH₂ |
| 26 | 54 | 0.49 | 0.6 | 2 | 25 | 1 | —(CH₂)₅— | | H | 5-O(CH₂)₂OCH₂Ph |
| 27 | 63 | 0.75 | 0.9 | 5 | 25 | 1 | —(CH₂)₅— | | H | 5-O(CH₂)₂OH |
| 28 | 55 | 0.85 | 1.0 | 1 | 25 | 2 | —(CH₂)₅— | | H | 5-OMe |
| 29 | 56 | 0.56 | 1.0 | 1 | 25 | 17 | —(CH₂)₅— | | H | 5-OMe |
| 30 | 57 | 2.66 | 3.2 | 9 | 25 | 1 | —(CH₂)₅— | | Me | 5-OMe |
| 31 | 58 | 2.66 | 3.2 | 9 | 25 | 1 | —(CH₂)₅— | | H | 5-OMe 8-Me |
| 32 | 59 | 1.75 | 2.1 | 5 | 25 | 1 | H | H | H | 5-OMe |
| 33 | 60 | 1.62 | 2.0 | 2 | 25 | 1 | Me | Me | H | 5-OMe |
| 34 | 61 | 1.29 | 1.55 | 5 | 25 | 2 | —(CH₂)₅— | | H | 8-OMe |
| 35[a] | 62 | 0.93 | 1.26 | 3 | 25 | 2 | —(CH₂)₅— | | H | 7-OMe |
| 36 | 64 | 1.58 | 1.9 | 6 | 25 | 0.5 | —(CH₂)₅— | | H | 6-Cl |
| 37 | 65-1 | 1.5 | 3.3 | 4 (+dichloromethane 4) | 25 | 1 | —(CH₂)₅— | | H | 5-OMe 6-Cl, 8-Cl |
| 38 | 65-2 | 1.5 | 3.3 | 4 | 25 | 0.5 | —(CH₂)₅— | | H | 5-OMe 6-Cl |
| 39 | 65-3 | 1.5 | 3.3 | 4 | 25 | 0.5 | —(CH₂)₅— | | H | 5-OMe 8-Cl |
| 40 | 68 | 1.5 | 3.3 | 4 (+dichloromethane 4) | 25 | 1 | —(CH₂)₅— | | H | 5-OH 6-Cl, 8-Cl |
| 41 | 67 | 1.5 | 3.3 | 4 | 25 | 0.5 | —(CH₂)₅— | | H | 5-OH 6-Cl |
| 42 | 66 | 1.5 | 3.3 | 4 | 25 | 0.5 | —(CH₂)₅— | | H | 5-OH 8-Cl |
| 43 | 69 | 1.05 | 1.2 | 4 | 25 | 1 | —(CH₂)₅— | | H | 5-OMe 8-NO₂ |
| 44 | 71 | 0.397 | 0.48 | 2 | 25 | 0.5 | —(CH₂)₅— | | H | 5-OH 8-SO₂NH₂ |
| 45 | 72 | 0.465 | 0.56 | 2.3 | 25 | 0.5 | —(CH₂)₅— | | H | 5-OH 8-SO₂NHMe |
| 46 | 73 | 0.52 | 0.62 | 2.3 | 25 | 0.5 | —(CH₂)₅— | | H | 5-OH 8-SO₂NMe₂ |
| 47 | 74 | 2.06 | 4.5 | 6 | 25 | 0.5 | —(CH₂)₅— | | H | 7-OMe |

| Compound of Example No. | A | position of HO₂C-A-O | Yield (%) |
|---|---|---|---|
| 1 | CH₂ | 6 | 86 |
| 2 | CH₂ | 7 | 98 |
| 3 | CH₂ | 7 | 82 |
| 4 | CH₂ | 7 | 93 |
| 5 | CH₂ | 7 | 95 |
| 6 | CH₂ | 7 | 87 |
| 7 | CH₂ | 7 | 96 |
| 8 | CH₂ | 7 | 91 |
| 9 | CH₂ | 7 | 88 |
| 10 | CH₂ | 7 | 90 |
| 11 | CH₂ | 7 | 93 |
| 12 | CH₂ | 7 | 86 |
| 13 | CH₂ | 7 | 95 |
| 14 | CH₂ | 7 | 94 |
| 15 | CH₂ | 7 | 90 |
| 16 | CH₂ | 7 | 81 |

TABLE 9-continued

| | | | |
|---|---|---|---|
| 17 | $CH_2$ | 7 | 92 |
| 18 | $CH_2$ | 7 | 88 |
| 19 | $CH_2$ | 7 | 100 |
| 20 | $CH_2$ | 7 | 95 |
| 21 | $CH_2$ | 7 | 92 |
| 22 | $CH_2$ | 7 | 90 |
| 23 | $CH_2$ | 7 | 83 |
| 24 | $CH_2$ | 7 | 89 |
| 25 | $CH_2$ | 7 | 93 |
| 26 | $CH_2$ | 7 | 93 |
| 27 | $CH_2$ | 7 | 90 |
| 28 | $CH(CH_3)$ | 7 | 80 |
| 29 | $(CH_2)_3$ | 7 | 45 |
| 30 | $CH_2$ | 7 | 79 |
| 31 | $CH_2$ | 7 | 96 |
| 32 | $CH_2$ | 7 | 95 |
| 33 | $CH_2$ | 7 | 97 |
| 34 | $CH_2$ | 7 | 90 |
| 35[a] | $CH_2$ | 8 | 87 |
| 36 | $CH_2$ | 7 | 99 |
| 37 | $CH_2$ | 7 | 88 |
| 38 | $CH_2$ | 7 | 97 |
| 39 | $CH_2$ | 7 | 95 |
| 40 | $CH_2$ | 7 | 95 |
| 41 | $CH_2$ | 7 | 96 |
| 42 | $CH_2$ | 7 | 90 |
| 43 | $CH_2$ | 7 | 98 |
| 44 | $CH_2$ | 7 | 74 |
| 45 | $CH_2$ | 7 | 95 |
| 46 | $CH_2$ | 7 | 91 |
| 47 | $CH_2$ | 5 | 95 |

[a] Natrium salt

TABLE 10

| Compd. of Ex. No. | M. p. °C. (recrystallized) | Molecular formula | Elemental analysis (found) C | H | Cl | $^1$H-NMR DMSO-$d_6$ δ ppm (J Hz) |
|---|---|---|---|---|---|---|
| 1 | 148-149 ether-hexane | $C_{16}H_{18}O_5$ | 66.19 (66.03) | 6.25 (6.35) | | 7.23(1H, dd, J=9.0 and 2.0), 7.16(1H, d, J=2.0), 6.99(1H, d, J=9.0), 4.67(2H, s), 2.74(2H, s), 2.1-1.1(10H, m) |
| 2 | 165-166 ether | $C_{16}H_{18}O_5$ | 66.19 (66.12) | 6.25 (6.29) | | 7.67(1H, d, J=9.0), 6.60(1H, dd, J=9.0 and 2.0), 6.49(1H, d, J=2.0), 4.78(2H, s), 2.69(2H, s), 2.0-1.2(10H, m) |
| 3 | 139-140 ether | $C_{18}H_{16}O_6$ | 65.85 (65.76) | 4.91 (5.51) | | acetone-$d_6$ 11.85(1H, s), 7.6-7.2(5H, m), 6.18(1H, d, J=2.0), 5.94(1H, d, J=2.0), 4.75(2H, s), 3.41(1H, d, J=16.5), 3.18(1H, d, J=16.5), 1.72(3H, s) |
| 4 | 175-177 ethanol | $C_{15}H_{16}O_6$ | 61.64 (61.62) | 5.52 (5.57) | | 12.03(1H, s), 6.01(2H, s), 4.75(2H, s), 2.91(2H, s), 2.1-1.5 (8H, m) |
| 5 | 163-164 ether-hexane | $C_{16}H_{18}O_6$ | 62.74 (62.74) | 5.92 (5.95) | | acetone-$d_6$ 12.0(1H, s), 6.05(1H, d, J=2.2), 6.97(1H, d, J=2.2), 4.77(2H, s), 2.71(2H, s), 2.2-1.2(10H, m) |
| 6 | 92-93 ethanol | $C_{18}H_{20}O_8$ $2H_2O$ | 54.00 (54.34) | 6.04 (6.11) | | 6.11(1H, d, J=2.0), 6.01(1H, d, J=2.0), 4.73(2H, s), 4.70(2H, s), 2.60(2H, s), 2.0-1.0(10H, m) |
| 7 | 151-152 ethanol | $C_{17}H_{20}O_5$ | 67.09 (67.05) | 6.62 (6.70) | | 6.42(1H, d, J=2.0), 6.37(1H, d, J=2.0), 4.75(2H, s), 2.63(2H, s) 2.50(3H, s), 2.0-1.2(10H, m) |
| 8 | 210-211 ethanol | $C_{17}H_{20}O_6$ | 63.74 (63.70) | 6.29 (6.28) | | acetone-$d_6$ 12.07(1H, s), 5.99(1H, s), 4.77(2H, s), 2.70(2H, s), 2.2-1.2(13H, s and m) |
| 9 | 172-173 ethyl acetate-hexane | $C_{16}H_{17}ClO_5$ | 59.17 (59.14) | 5.28 (5.23) | 10.92 (10.75) | 6.66(1H, d, J=2.4), 6.53(1H, d, J=2.4), 4.82(2H, s), 2.73(2H, s), 1.9-1.1(10H, m) |
| 10 | 253-254 ethanol | $C_{16}H_{16}Cl_2O_5$ | 53.50 (53.29) | 4.49 (4.56) | 19.74 (19.84) | 13.3(1H, bs), 6.75(1H, s), 4.98(2H, s), 2.77(2H, s), 1.9-1.15(10H, m) |
| 11 | 215-217 ether-hexane | $C_{16}H_{16}Cl_2O_5$ | 53.50 (53.66) | 4.49 (4.55) | 19.74 (19.76) | 6.86(1H, s), 4.98(2H, s), 2.80(2H, s), 1.95-1.1(10H, m) |
| 12 | 232-233 ethyl acetate | $C_{11}H_{10}O_6$ | 55.47 (55.24) | 4.23 (4.14) | 10.92 (10.75) | 13-12(1H, b), 12.1(1H, s), 6.02(2H, s), 4.73(2H, s), 4.46(2H, t, J=6.5), 2.79(2H, t, J=6.5) |
| 13 | 234-235 acetone | $C_{11}H_{10}O_5$ | 59.46 (59.15) | 4.54 (4.86) | | 7.68(1H, d, J=9.0), 6.63(1H, dd, J=9.0 and 2.0), 6.48(1H, d, J=2.0), 4.74(2H, s), 4.49(2H, t, J=7.0), 2.69(2H, t, J=7.0) |

| Compd. of Ex. No. | M. p. °C. (recrystallized) | Molecular formula | Elemental analysis C | H | $^1$H-NMR DMSO-$d_6$ δ ppm (J Hz) |
|---|---|---|---|---|---|
| 14 | 189-190 ethyl acetate | $C_{13}H_{14}O_5$ | 62.39 (62.35) | 5.64 (5.68) | 7.65(1H, d, J=9.0), 6.58(1H, dd, J=9.0 and 2.0), 6.43(1H, d, J=2.0), 4.73(2H, s), 2.19(2H, s), 1.38(6H, s) |
| 15 | 207-208 ethanol | $C_{12}H_{12}O_5$ | 61.01 (60.81) | 5.12 (5.18) | 7.68(1H, d, J=9.0), 6.60(1H, dd, J=9.0 and 2.0), 6.47(1H, d, J=2.0), 4.75(2H, s), 4.60(1H, m), 2.7-2.45(2H, m), 1.42(3H, d, J=7.0) |
| 16 | 192-193 ethanol | $C_{17}H_{14}O_5$ | 68.45 (68.15) | 4.73 (4.78) | 7.77(1H, d, J=9.0), 7.7-7.5(5H, m), 6.70(1H, dd, J=9.0 and 2.0), 6.59(1H, d, J=2.0), 5.65(1H, dd, J=12.0 and 3.0), 4.80(2H, s), 3.70(1H, dd, J=16.5 and 12.0), 2.75(1H, dd, J=16.5 and 3.0) |
| 17 | 202-203 ether | $C_{13}H_{14}O_6$ | 58.64 (58.55) | 5.30 (5.43) | 12.07(1H, s), 6.00(2H, s), 4.74(2H, s), 2.82(2H, s), 1.40(6H, s) |

TABLE 10-continued

| | M. p. °C. (recrystallized) | Molecular formula | Elemental analysis C | Elemental analysis H | | $^1$H-NMR DMSO-$d_6$ δ ppm (J Hz) |
|---|---|---|---|---|---|---|
| 18 | 210-211 ethanol | $C_{18}H_{20}O_6$ | 59.34 (59.10) | 5.53 (5.57) | | acetone-$d_6$ 7.53(1H, d, J=9.0), 6.71(1H, d, J=9.0), 4.89(2H, s), 4.74(2H, s), 2.71(2H, s), 2.1-1.2(10H, m) |
| 19 | 168-169 ether-hexane | $C_{16}H_{18}O_6$ | 62.74 (62.41) | 5.92 (5.90) | | acetone-$d_6$ 7.49(1H, d, J=9.0), 6.53(1H, d, J=9.0), 4.80(2H, s), 2.68(2H, s), 2.0-1.3(10H, m) |
| 20 | 192-193 ethanol | $C_{16}H_{18}O_6$ | 62.74 (62.59) | 5.92 (5.92) | | 6.18(1H, d, J=2.0), 6.02(1H, d, J=2.0), 4.75(2H, s), 3.77(3H, s) 2.67(2H, s), 2.0-1.4(8H, m) |
| 21 | 188-189 ethyl acetate | $C_{17}H_{20}O_6$ | 63.74 (63.63) | 6.29 (6.35) | | 6.15(1H, d, J=2.0), 6.05(1H, d, J=2.0), 4.74(2H, s), 3.73(3H, s), 2.55(2H, s), 2.0-1.2(10H, m) |
| 22 | 175-176 ethyl acetate | $C_{18}H_{22}O_6$ | 64.66 (64.39) | 6.63 (6.68) | | acetone-$d_6$ 6.16(1H, d, J=2.0), 6.08(1H, d, J=2.0), 4.73(2H, s), 4.04(2H, q, J=7.0), 2.53(2H, s), 2.0-1.2(13H, m) |
| 23 | 192-193 ethanol | $C_{23}H_{24}O_6$ | 69.68 (69.50) | 6.10 (6.15) | | acetone-$d_6$ 7.70-7.25(5H, m), 6.30(1H, d, J=2.0), 6.13(1H, d, J=2.0), 5.17(2H, s), 4.73(2H, s), 2.60(2H, s), 2.1-1.2(10H, m) |
| 24 | 150-151 ether | $C_{18}H_{24}O_6$ | 65.50 (65.50) | 6.94 (7.04) | | acetone-$d_6$ 6.18(1H, d, J=2.0), 6.08(1H, d, J=2.0), 4.72(2H, s), 4.58(1H, m), 2.53(2H, s), 2.0-1.1(m), 1.32(d, J=7.0)(16H) |
| 25 | 177-178 ethyl acetate | $C_{19}H_{22}O_6$ | 65.89 (65.73) | 6.40 (6.32) | | 13.11(1H, b), 6.20-5.95(3H, m), 5.61(1H, bd, J=17.2), 5.24(1H, bd, J=10.6), 4.74(2H, s), 4.54(2H, bs), 2.56(2H, s), 1.95-1.10(10H, m) |
| 26 | 174 ethyl acetate | $C_{25}H_{28}O_7$ | 68.17 (67.95) | 6.41 (6.36) | | 7.37-7.30(5H, m), 6.18(1H, d, J=2.2), 6.07(1H, d, J=2.2), 4.75(2H, s), 4.65(2H, s), 4.13(2H, bt), 3.77(2H, bt), 2.58(2H, s), 1.9-1.2(10H, m) |
| 27 | 120-122 ether | $C_{18}H_{22}O_7$ | 61.71 (61.67) | 6.33 (6.39) | | 6.18(1H, d, J=2.0), 6.07(1H, d, J=2.0), 4.76(2H, s), 3.99(2H, t, J=5.0), 3.70(2H, t, J=5.0), 3.45(1H, b), 2.57(2H, s), 1.9-1.2(10H, m) |
| 28 | 191-193 acetone-hexane | $C_{18}H_{22}O_6$ | 64.66 (64.48) | 6.63 (6.67) | | acetone-$d_6$ 6.15(1H, d, J=2.0), 6.03(1H, d, J=2.0), 4.91(1H, q, J=6.5), 3.79(3H, s), 2.53(2H, s), 1.58(3H, d, J=6.5), 2.1-1.1(10H, m) |
| 29 | 167-169 acetone-ethyl acetate-ether | $C_{19}H_{24}O_6$ | 65.50 (65.49) | 6.94 (7.00) | | acetone-$d_6$ 6.14(2H, s), 4.10(2H, t, J=6.4), 3.80(3H, s), 2.53(2H, s), 2.47(2H, t, J=6.3), 2.63-1.15(12H, m) |
| 30 | 111-112 ether-hexane | $C_{18}H_{22}O_6$ 1/2$H_2O$ | 62.96 (62.87) | 6.75 (6.63) | | CDCl$_3$ 9.5(1H, bs), 6.14(1H, d, J=2.0), 6.03(1H, d, J=2.0), 4.70(2H, s), 3.83(3H, s), 2.55(1H, q, J=7.0), 2.1-1.2(10H, m), 1.12(3H, d, J=7.0) |
| 31 | 203-204 ethyl acetate | $C_{18}H_{22}O_6$ | 64.66 (64.37) | 6.63 (6.62) | | 6.17(1H, s), 4.80(2H, s), 3.74(3H, s), 2.53(2H, s), 2.03(3H, s), 2.0-1.2(10H, m) |
| 32 | 230-232 (decomposition) ethanol | $C_{12}H_{12}O_6$ | 57.14 (57.16) | 4.79 (4.80) | | 6.19(1H, d, J=2.2), 6.07(1H, d, J=2.2), 4.75(2H, s), 4.39(2H, t, J=6.4), 3.76(3H, s), 2.59(2H, t, J=6.4) |
| 33 | 220-222 ethyl acetate | $C_{14}H_{16}O_6$ | 59.99 (59.82) | 5.75 (5.75) | | 6.17(1H, d, J=2.0), 6.02(1H, d, J=2.0), 4.75(2H, s), 3.77(3H, s), 2.58(2H, s), 1.34(6H, s) |
| 34 | 174-175 ether | $C_{17}H_{20}O_6$ | 63.74 (63.59) | 6.29 (6.30) | | acetone-$d_6$ 7.49(1H, d, J=9.0), 6.65(1H, d, J=9.0), 4.83(2H, s), 3.90(3H, s), 2.67(2H, s), 2.0-1.2(10H, m) |

| Compd. of Ex. No. | M. p. °C. (recrystallized) | Molecular formula | Elemental analysis C | Elemental analysis H | Elemental analysis Cl | Elemental analysis Na | $^1$H-NMR DMSO-$d_6$ δ ppm (J Hz) |
|---|---|---|---|---|---|---|---|
| 35 | 269-270 ethanol | $C_{17}H_{19}O_6Na$ | 59.64 (59.59) | 5.59 (5.67) | | 6.72 (6.89) | acetone-$d_6$ 7.55(1H, d, J=9.0), 6.75(1H, d, J=9.0), 4.64(2H, s), 3.95(3H, s), 2.68(2H, s), 2.1-1.2(10H, m) |
| 36 | 221-222 ethanol | $C_{16}H_{17}ClO_5$ | 59.17 (59.30) | 5.28 (5.33) | 10.92 (11.06) | | 7.67(1H, s), 6.70(1H, s), 4.93(2H, s), 2.73(2H, s), 2.0-1.2(10H, m) |
| 37 | 150-151 ether-hexane | $C_{17}H_{18}Cl_2O_6$ | 52.46 (52.34) | 4.66 (4.71) | 18.22 (18.46) | | acetone-$d_6$ 4.77(2H, s), 3.82(3H, s), 2.74(2H, s), 2.1-1.3(10H, m) |
| 38 | 196-197 ethanol | $C_{17}H_{19}ClO_6$ | 57.55 (57.52) | 5.40 (5.36) | 9.99 (9.83) | | acetone-$d_6$ 6.49(1H, s), 4.90(2H, s), 3.82(3H, s), 2.15(2H, s), 2.1-1.3(10H, m) |
| 39 | 201-202 ethanol | $C_{17}H_{19}ClO_6$ | 57.55 (57.30) | 5.40 (5.56) | 9.99 (10.08) | | acetone-$d_6$ 6.38(1H, s), 4.94(2H, s), 3.83(3H, s), 2.60(2H, s), 2.1-1.3(10H, m) |
| 40 | 154-155 ether-hexane | $C_{16}H_{18}Cl_2O_6$ | 51.22 (51.08) | 4.30 (4.36) | 18.90 (19.14) | | acetone-$d_6$ 12.47(1H, b), 8-6(1H, b), 4.78(2H, s), 2.90(2H, s), 2.2-1.2(10H, m) |
| 41 | 213-214 ethanol | $C_{16}H_{17}ClO_6$ | 56.40 (56.32) | 5.03 (5.02) | 10.40 (10.62) | | acetone-$d_6$ 12.5(1H, s), 6.23(1H, s), 6.1-5.0(1H, b), 4.90(2H, s), 2.77(2H, s), 2.1-1.2(10H, m) |
| 42 | 195-196 ethanol | $C_{16}H_{17}ClO_6$ | 56.40 (56.19) | 5.03 (5.01) | 10.40 (10.54) | | acetone-$d_6$ 12.07(1H, s), 6.14(1H, s), 6.0-5.0(1H, b), 4.88(2H, s), 2.78(2H, s), 2.1-1.2(10H, m) |

| Compd. of Ex. No. | M. p. °C. (recrystallized) | Molecular formula | Elemental analysis C | Elemental analysis H | Elemental analysis Cl | Elemental analysis S | $^1$H-NMR DMSO-$d_6$ δ ppm (J Hz) |
|---|---|---|---|---|---|---|---|
| 43 | 243-245 ethanol | $C_{17}H_{19}NO_8$ | 55.89 (56.18) | 5.24 (5.56) | 3.83 (3.63) | | 6.44(1H, s), 5.01(2H, s), 3.87(3H, s), 2.68(2H, s), 2.1-1.2(10H, m) |
| 44 | 238-240 (decomposition) ethanol-water | $C_{17}H_{21}NO_8S$ 1/2$H_2O$ | 51.12 (49.99) | 5.30 (5.43) | 3.51 (3.43) | 8.03 7.85 | 13.6(1H, b), 7.11(2H, s), 6.34(1H, s), 4.99(2H, s), 3.86(3H, s), 2.59(2H, s), 2.0-1.1(10H, m) |
| 45 | 272-274 (decomposition) ethanol | $C_{18}H_{23}NO_8S$ 1/2$H_2O$ | 51.18 (51.44) | 5.72 (5.61) | 3.31 (3.24) | 7.59 (7.15) | 13.6(1H, s), 6.33(1H, s), 5.02(2H, s), 6.83(1H, q, J=5.4), 3.86(3H, s), 2.62(2H, s), 2.50(3H, d, J=5.4), 2.0-1.1(10H, m) |
| 46 | 238-239 ethanol | $C_{19}H_{25}NO_8S$ | 53.39 (53.18) | 5.89 (5.73) | 3.28 (3.22) | 7.50 (7.22) | 13.3(1H, s), 6.21(1H, s), 5.03(2H, s), 3.82(3H, s), 2.79(6H, s), 2.61(2H, s), 1.95-1.13(10H, m) |
| 47 | 150-151 ether | $C_{17}H_{20}O_6$ | 63.74 (63.70) | 6.29 (6.27) | | | acetone-$d_6$ 6.28(2H, s), 4.76(2H, s), 3.89(3H, s), 2.68(2H, s), 2.1-1.2(10H, m) |

Example 48

2-{(5-Methoxy-3,4-dihydro-4-oxospiro[2H-1-benzopyran-2,1'-cyclohexan]-7-yl)amino }acetic acid A mixture of (4'-amino-2',6'-dimethoxyphenyl) ethanone (prepared in Preparation 76) (1.185 g, 6.08 mmol), dry dichloromethane (30 ml), triethylamine (0.55 g, 5.5 mmol, and trifluoroacetic acid anhydride (1.15 g, 5.48 mmol)) is stirred for 1.5 hours under ice-cooling, which is followed by the addition of dichloromethane. The mixture is washed with dilute hydrochloric acid and then water, dried, and the solvent is removed by distillation. The residue is placed on a silica gel column and eluted with a mixtue of dichloromethane and ethyl acetate (1:1) to yield a crude product. Recrystallization from a mixture of diethyl ether and hexane gives (4'-trifluoroacetylamino-2',6'-dimethoxyphenyl)ethanone as a crystalline solid (1.67 g, yield 85%, m.p.=172°-173° C.).

Elemental analysis (for $C_{12}H_{12}F_3NO_4$)
Calcd.: C, 49.49; H, 4.15; N, 4.81
Found: C, 49.51; H, 4.19; N, 5.05
$^1$H-NMR (CDCl$_3$) δppm: 8.42(1H,b), 6.83(2H,s), 3.78(6H,s), 2.46(3H,s).

A mixture of above (4'-trifluoroacetylamino-2',6'-dimethoxyphenyl)ethanone (1.73 g, 5.95 mmol), anhydrous DMF (60 ml), anhydrous potassium carbonate (0.50 g, 3.62 mmol), and methyl bromoacetate (0.55 g, 3.74 mmol) is heated at 70 ° C. for 45 minutes with stirring. The mixture is diluted with water and extracted with ethyl acetate. The ethyl acetate layer is washed with water, dried, and the solvent is removed by distillation. The residue is placed on a silica gel column and eluted with a mixture of dichloromethane and ethyl acetate (15:1) to yield a crude product. Recrystallization from hexane gives methyl (4'-acetyl-3',5'-dimethoxyphenyl-N-trifluoroacetylamino) acetate (1.26 g, yield 91%, m.p.=108°-109° C.).

$^1$H-NMR (CDCl$_3$) δppm: 6.60(2H,s), 4.37(2H,s), 3.80(9H,s), 2.47(3H,s).

To a solution of above methyl (4'-acetyl-3',5'-dimethoxyphenyl-N-trifluoroacetylamino)acetate (1.2 g, 3.36 mmol) in anhydrous dichloromethane (50 ml) is added dropwise 2M boron trichloride in dichloromethane (3.89 ml, 7.78 mmol) at −30° C. After 1.5 hours stirring at room temperature, ice-cold water is added to the mixture. The mixture is then extracted with dichloromethane. The extract is washed with water, dried, and the solvent is removed by distillation. The residue is placed on a silica gel column and eluted with a mixture of dichloromethane and ethyl acetate (20:1) to obtain a crystalline product (1.04 g, yield 90%, m.p.=79°-80° C.). The crystalline product (0.95 g) is dissolved in absolute methanol (40 ml), and 0.2N sodium methylate solution in methanol (10.65 ml) is added dropwise to it at 0° C. After 20 minutes stirring, the solvent is removed by distillation. The residue is placed on a silica gel column and eluted with a mixture of dichloromethane and ethyl acetate (20:1) to obtain methyl (4'-acetyl-3'-hydroxy-5'-methoxyphenylamino)acetate (0.388 g, yield 56%, m.p.=114°-115° C.).

Elemental analysis (for $C_{12}H_{15}NO_5$)
Calcd.: C, 56.91; H, 5.97; N, 5.53
Found: C, 56.92; H, 5.95; N, 5.73
$^1$H-NMR (CDCl$_3$) δppm: 14.2(1H,b), 5.65(1H,d,J=1.5),
5.55(1H,d,J=1.5), 3.90(2H,s),
3.81(6H,s), 2.55(3H,s).

A mixture of methyl (4'-acetyl-3'-hydroxy-5'-methoxyphenylamino)acetate obtained above (0.388 g, 1.53 mmol), absolute ethanol (30 ml), and cyclohexanonepyrrolidine enamine (0.462 g, 3.02 mmol) is heated to reflux for 2 hours under argon gas, and the solvent is removed. The residue is dissolved in ethyl acetate. The solution is washed with diluted HCl and then water, dried, and the solvent is removed. The residue is placed on a silica gel column and eluted with a mixture of dichloromethane and ethyl acetate (1:1). The starting material (0.06 g, 15.5%) is recovered from the earlier fractions. From the succeeding fractions, methyl 2-{(5-methoxy-3,4-dihydro-4-oxospiro[2H-1-benzopyran-2,1'-cyclohexan]-7-yl)amino}acetate is obtained as a crystalline solid (0.481 g, 82%, m.p.=168°-169° C.).

Elemental analysis (for $C_{18}H_{23}NO_5$)
Calcd.: C, 64.85; H, 6.95; N, 4.20
Found: C, 64.57; H, 7.00; N, 4.53
$^1$H-NMR (CDCl$_3$) δppm: 5.71(1H,d,J=2.2),
5.69(1H,d,J=2.2),
5.7-4.6(1H,b), 3.95(2H,s),
3.86(3H,s), 3.82(3H,s),
2.59(2H,s), 2.1-1.2(10H,m).

A mixture of methyl 2-{(5-methoxy-3,4-dihydro-4-oxospiro[2H-1-benzopyran-2,1'-cyclohexan ]-7-yl)amino} acetate obtained above (0.394 g, 1.18 mmol), 1N sodium hydroxide (1.19 ml, 1.19 mmol), and ethanol (10 ml ) is stirred at room temperature for one hour. Ethanol is distilled under reduced pressure, and the residue is dissolved in water. The aqueous solution is washed with ethyl acetate, and filtered to remove insoluble substances. The filtrate is adjusted to pH 5-6 with dilute HCl. The resulting crystalline precipitate is separated by filtration, washed with water and dried to yield the title compound as a crystalline solid (0.351 g, 93%, m.p.=112°-113° C.).

Elemental analysis (for $C_{17}H_{21}NO_5$)
Calcd.: C, 63.94; H, 6.63; N, 4.39
Found: C, 63.82; H, 6.60; N, 4.23
$^1$H-NMR (d$_6$-acetone) δppm: 5.98(1H,d,J=2.2),
5.95(1H,b),
5.79(1H,d,J=2.2),
4.03(2H,d,J=5.2),
3.74(3H,s), 2 45(2H,s),
2.1-1.2(10H,m).

Example 49

2-{(5-Hydroxy-3,4-dihydro-4-oxospiro[2H-1-benzothiine-2,1'-cyclohexan]-7-yl)oxy }acetic acid (1) A mixture of 5,7-dihydroxy-spiro [2H-1-benzothiine-2,1'-cyclohexan]-4(3H)-one (prepared in Preparation 79) (0.47 g, 1.78 mmol ), ethyl bromoacetate (0.297 g, 1.78 mmol), anhydrous potassium carbonate (0.368 g, 2.67 mmol), and dry acetonitrile (5 ml) is stirred overnight at room temperature. The mixture is stirred at 35° C. for additional 5 hours. The reaction mixture is filtered to remove inorganic materials. The solvent is removed by distillation from the filtrate. The residue is placed on a silica gel column and eluted with a mixture of dichloromethane and ethyl acetate (9:1) to obtain ethyl 2-{(5-hydroxy-3,4-dihydro-4-oxospiro[2H-1-benzothiine-2,1'-cyclohexan]-7-yl)oxy}acetate as a crystalline solid (0.57 g, 91.5%). Recrystallization from diethyl ether gives a product having a melting point of 87°-88° C.

Elemental analysis (for $C_{18}H_{22}O_5S$)
Calcd.: C, 61.69; H, 6.33; S, 9.15

Found C, 61.73; H, 6.45; S, 8.95
1H-NMR (CDCl3) δppm: 13.05(1H,s), 6.36(1H,d,J=2.4),
6.09(1H,d,J=2.4), 4.61(2H,s),
4.28(2H,q,J=7), 2.90(2H,s),
2.0-1.2(10H,m), 1.30(3H,t,J=7).

(2) A mixture of the crystalline solid (0.11 g, 0.314 mmol ) obtained above (1), 1N-sodium hydroxide (0.76 ml, 0.76 mmol), and ethanol (1 ml) is stirred at room temperature for 2 hours. The mixture is made acidic with dilute HCl. The resulting crystalline precipitates are separated by filtration, washed with water, dried and recrystallized from diethyl ether to yield the title compound as a crystalline solid (0.092 g, 90%, m.p.=189°-190° C.).

Elemental analysis (for $C_{16}H_{18}O_5S$)
Calcd.: C, 59.61; H, 5.63; S, 9.94
Found: C, 59.39; H, 5.85; S, 9.82
1H-NMR (d6-DMSO) δppm: 13.03(1H,s), 6.42(1H,d,J=2.4),
6.19(1H,d,J=2.4), 4.78(2H,s),
2.98(2H,s), 1.9-1.1(10H,m).

Example 50

2-{(5-Methoxy-3,4-dihydro-4-oxospiro[2H-1-benzothiin-2,1'-cyclohexan]-7-yl)oxy}acetic acid A mixture of ethyl 2-{(5-hydroxy-3,4-dihydro-4-oxospiro[2H-1-benzothiin-2,1'-cyclohexan]-7-yl)oxy}acetate (prepared in Example 49 (1)) (0.129 g, 0.369 mmol), methyl iodide (0.078 g, 0.56 mmol), anhydrous potassium carbonate (0.102 g, 0.74 mmol), and dry DMF (1 ml) is stirred overnight at room temperature and the solvent is removed by distillation. The residue is dissolved in diethyl ether. The solution is washed with saturated brine, dried and concentrated. The residue is placed on a silica gel column and eluted with a mixtue of dichloromethane and ethyl acetate (9:1) to obtain a product as a crystalline solid (0.118 g, 88%). Recrystallization from ethanol gives a product having a melting point of 121°-122° C.).

Elemental analysis (for $C_{19}H_{24}O_5S$)
Calcd.: C, 62.62; H, 6.64; S, 8.80
Found: C, 62.40; H, 6.59; S, 8.53
1H-NMR (CDCl3) δppm: 6.29(2H,s), 4.62(2H,s ),
4.26(2H,q,J=7), 3.87(3H,s ),
2.86(2H,s), 2.2-1.2(10H,m),
1.30(3H,t,J=7).

A mixture of the above crystalline solid (0.085 g, 0.23 mmol), 1N-sodium hydroxide (0.28 ml, 0.28 mmol), and ethanol (2 ml) is stirred at room temperature for 0.5 hours. The mixture is made acid with dilute HCl and distilled under reduced pressure to remove ethanol. The residue is extracted with a mixture of diethyl ether and dichloromethane (1:1). The organic layer is washed with saturated brine, dried, and the solvent is removed. The crystalline residue is washed with diethyl ether and recrystallized from ethanol to yield the title compound (0.070 g, 89.4%, m.p.=195°-196° C.).

Elemental analysis (for $C_{17}H_{20}O_5S$)
Calcd.: C, 60.70; H, 5.99; S, 9.53
Found: C, 60.59; H, 5.96; S, 9.29
1H-NMR (d6-DMSO) δppm: 13.14(1H,s), 6.40(1H,d,J=2.2),
6.38(1H,d,J=2.2), 4.80(2H,s),
3.77(3H,s ), 2.80(2H,s),
1.9-1.1(10H,m).

Example 51

2-{(5-Hydroxy-4-oxo-spiro[1,2,3,4-tetrahydroquinoline-2,1'-cyclohexan]-7-yl)oxy}acetic acid (1) A mixture of 5,7-dihydroxyspiro[1,2,3,4-tetrahydroquinoline-2,1'-cyclohexan]-4-one (prepared in Preparation 81) (0.247 g, 1.0 mmol), ethyl bromoacetate (0.184 g, 1.10 mmol), anhydrous potassium carbonate (0.207 g, 1.5 mmol), and dry acetonitrile (4 ml) is stirred at room temperature for 4 hours. The solvent is removed under reduced pressure and the residue is extracted with ethyl acetate and water. The ethyl acetate layer is separated, washed with water, dried, and the solvent is removed. The residue is placed on a silica gel column and eluted with a mixture of acetone and dichloromethane (1:10) to obtain a crude product. Recrystallization from a mixture of diethyl ether and hexane gives ethyl 2-{(5-hydroxy-4-oxospiro [1,2,3,4-tetrahydroquinoline-2,1'-cyclohexan]-7-yl)oxy}acetate (0.265 g, 79%, m.p.=134°-135° C.).

Elemental analysis (for $C_{18}H_{23}NO_5$)
Calcd.: C, 64.85; H, 6.95; N, 4.20
Found: C, 64.52; H, 7.01; N, 4.15
1H-NMR (CDCl3) δppm: 12.47(1H,s), 5.70(1H,d,J=2.4),
5.64(1H,d,J=2.4), 4.58(2H,s),
4.45(1H,b), 4.28(2H,q,J=7),
2.60(2H,s), 1.9-1.2(10H,m),
1.31(3H,t,J=7).

(2) A mixture of the product obtained in (1) (0.103 g, 0.31 mmol), 0.2N sodium hydroxide (1.85 ml, 0.37 mmol), and ethanol (2 ml) is stirred at room temperature for 0.75 hours. The mixture is made acidic with dilute HCl and distilled under reduced pressure to remove ethanol. The residue is extracted with ethyl acetate. The organic layer is separated, washed with saturated brine, dried, and the solvent is removed to obtain crystalline residue. The residue is washed with diethyl ether., and recrystallized from ether to obtain the title compound (0.090 g, 95%, m.p.=177°-178° C.).

Elemental analysis (for $C_{16}H_{19}NO_5 \cdot \frac{1}{2}H_2O$)
Calcd.: C, 61.14; H, 6.41; N, 4.45
Found: C, 61.36; H, 6.50; S, 4.33
1H-NMR (d6-DMSO) δppm: .10(1H,b), 12.46(1H,s),
6.87(1H,bs), 5.83(1H,d,J=2.2),
5.52(1H,d,J=2.2), 4.62(2H,s),
2.51(2H,s), 1.80-1.20(10H,m).

Example 52

2-{(5-Methoxy-4-oxospiro[1,2,3,4-tetrahydroquinoline-2,1'-cyclohexan]-7-yl)oxy}acetic acid (1) A mixture of ethyl 2-{(5-hydroxy-4-oxospiro [1,2,3,4-tetrahydroquinoline-2,1'-cyclohexan]-7-yl)oxy}acetate (prepared in Example 51 (1)) (0.15 g, 0.45 mmol), methyl iodide (0.071 g, 0.50 mmol), anhydrous potassium carbonate (0.094 g, 0.68 mmol), and dry DMF (4 ml) is stirred at 40° C. for 9 hours. After the addition of methyl iodide (0.14 g, 1.0 mmol), the stirring is continued for additional 4 hours. The solvent is removed by distillation and the residue is dissolved in ethyl acetate. The solution is washed with saturated brine, dried, and the solvent is removed. The residue is placed on a silica gel column and eluted with a mixture of ethyl acetate and dichloromethane (1:10). The earlier fractions containing oily materials are discarded. From the succeeding fractions, the desired product is obtained as a crystalline solid (0.067 g, 43%, m.p=158°-159° C.).
1H-NMR (CDCl3) δppm: 5.83(1H,d,J=2.4), 5.62(1H,d,J=2.4), 4.58(2H,s),
4.29(2H,q,J=7), 3.84(3H,s),
2.57(2H,s), 2.9–1.2(10H,m),
1.31(3H,t,J=7).

(2) A mixture of the above crystalline solid (0.060 g, 0.173 mmol), 0.2N sodium hydroxide (1 ml, 0.2 mmol), and ethanol (1 ml) is stirred at room temperature for 1.75 hours. The mixture is made acid with dilute HCl. Ethanol is removed under reduced pressure to yield a crystalline residue. The residue is dissolved in acetone and the mixture is filtered to remove insoluble materials. The filtrate is distilled under reduced pressure. The residue is recrystallized from a mixture of acetone and diethyl ether to yield the title compound as a crystalline solid (0.031 g, 56%, m.p.=241°–242° C.).

Elemental analysis (for $C_{17}H_{21}NO_5 \cdot \frac{1}{2}H_2O$)
Calcd.: C, 58.94; H, 6.98; N, 4.04
Found: C, 58.64; H, 6.75; S, 4.04
$^1$H-NMR (d$_6$-DMSO) δppm: 13.10(1H,b), 6.65(1H,bs),
5.94(1H,d,J=2.2),
5.69(1H,d,J=2.2), 4.61(2H,s ),
3.66(3H,s), 2.33(2H,s),
1.80–1.20(10H,m).

Example 53

{(5-Methoxy-4-chlorospiro[2H-1-benzopyran-2,1'-cyclohexan]-7-yl)oxy}acetic acid

{(5-Methoxy-3,4-dihydro-4-oxospiro[2H-1-benzopyran-2,1'-cyclohexan]-7-yl)oxy}acetic acid (prepared in Example 21) (0.29 g, 0.91 mmol) is reacted with an excess of diazomethane in diethyl ether. The mixture is distilled to remove diazomethane and ether. To the residue is added oxalyl chloride (0.463 g, 3.65 mmol) and dry benzene (10 ml), and the mixture is heated to reflux for 3.5 hours. The solvent is removed under reduced pressure. The residue is placed on a silica gel column and eluted with a mixture of ethyl acetate and hexane (1:2) to obtain methyl {(5-methoxy-4-chlorospiro[2H-1-benzopyran-2,1'-cyc lohexan]-7-yl)oxy} acetate as a crystalline solid (0.30 g, 93%).

A mixture of the obtained ester (0.30 g, 0.85 mmol), 1N sodium hydroxide (1 ml, 1.0 mmol), and ethanol (2 ml) is stirred at room temperature for 0.5 hours. The reaction mixture is made acidic with 1N HCl and distilled under reduced pressure at room temperature to remove ethanol. The residue is extracted with diethyl ether. The extract is washed with saturated brine, dried, and the solvent is removed under reduced pressure. The residue is treated with diethyl ether and recrystallized from 80% ethanol to obtain the title compound (0.185 g, 64.5%, m.p.=132°–133° C.).

Elemental analysis (for $C_{17}H_{19}ClO_5$)
Calcd.: C, 60.27; H, 5.65; Cl. 10.46
Found: C, 60.13; H, 5.75; Cl, 10.18
$^1$H-NMR (d$_6$-DMSO) δppm: 13.05(1H,b), 6.22(1H,d,J=2.4),
6.12(1H,d,J=2.4), 5.75(1H,s),
4.70(2H,s), 3.76(3H,s),
1.85–1.1(10H,m).

Example 54

{(5-Methoxy-3,4-dihydrodispiro[2H-1-benzopyran-2,1'-cyclohexan-4,2''-[1,3]dithiolan ]-7-yl)oxy}acetic acid A mixture of ethyl {(5-methoxy-3,4-dihydro-4-oxospiro[2H-1-benzopyran-2,1'-cyclohexan]-7-yl)oxy}acetate (prepared in Preparation 49) (0.5 g, 1.44 mmol), ethanedithiol (0.149 g, 1.59 mmol), dry benzene (10 ml), and p-toluenesulfonic acid (0.013 g, 0.076 mmol) is heated to reflux for 12 hours under conditions for azeotropic dehydration. The solvent is removed under reduced pressure. The residue is applied to a silica gel column and eluted with a mixture of ethyl acetate and dichloromethane (1:9). The eluate is applied to a Lober column and eluted with a mixture of ethyl acetate and hexane (1:2) to obtain ethyl {(5-methoxy-3,4-dihydrodispiro[2H-1-benzopyran-2,1'-cyclohexan-4,2''-[1,3]dithiolan]-7-yl)oxy}acetate as an oil (0.50 g, 82.1%). A mixture of the ester (0.49 g, 1.16 mmol), 1N sodium hydroxide (1.27 ml, 1.27 mmol), and ethanol (5 ml) is stirred at room temperature for 0.5 hours. The reaction mixture is made acid with 1N HCl and distilled under reduced pressure at room temperature to remove ethanol. The residue is extracted with diethyl ether. The extract is washed with saturated brine, dried, and the solvent is removed under reduced pressure. The residue is treated with a mixture of diethyl ether and hexane to obtain the title compound as a crystalline soild (0.43 g, 93.7%). Recrystallization from ethyl acetate gives a product having a melting point of 189°–190° C.

Elemental analysis (for $C_{19}H_{24}O_5S_2$)
Calcd.: C, 57.55; H, 6.10; S, 16.17
Found: C, 57.39; H, 5.95; S, 16.46
$^1$H-NMR (d$_6$-DMSO) δppm: 13.0(1H,b), 6.15(1H,d,J=2.4),
5.88(1H,d,J=2.4), 4.62(2H,s),
3.77(3H,s), 3.6–3.3(4H,m),
2.55(2H,s), 1.8–1.2(10H,m).

Example 55

2-{N-acetyl-(5-methoxy-3,4-dihydro-4-oxospiro [2H-1-benzopyran-2,1'-cyclohexan-7-yl)amino}acetic acid To a solution of 2-{(5-methoxy-3,4-dihydro-4-oxospiro[2H-1-benzopyran-2,1'-cyclohexan-7 -yl)amino}acetic acid (prepared in Example 48) (0.204 g, 0.64 mmol) in pyridine (3 ml) is added acetyl chloride (0.126 g, 1.61 mmol) and the mixture is stirred two overnights at room temperature. To the reaction mixture is added ice and dilute hydrochloric acid, and the mixture is extracted with ethyl acetate. The extract is washed with water, dried, and the solvent is removed. The residue is applied to a silica gel column and eluted with a mixture of ethyl acetate, dichloromethane and acetic acid (200:800:1). The eluate is distilled under reduced pressure and the residue is dissolved in ethyl acetate. The solution is washed with water, dried, and the solvent is removed to obtain the title compound as an amorphous substance (0.080 g, 33%).

Elemental analysis (for $C_{19}H_{23}NO_6 \cdot 5/4H_2O$)
Calcd.: C, 59.44; H, 6.69; N, 3.65
Found: C, 59.70; H, 6.42; N, 3.61
$^1$H-NMR (CDCl$_3$) δppm: 6.56(1H,d,J=1.6),
6.46(1H,d,J=1.6), 4.9(1H,b),
4.38(2H,s), 3.90(3H,s),
2.69(2H,s), 2.06(3H,s),
2.1–1.2(10H,m).

Example 56

Pivaloyloxymethyl 2-{(5-methoxy-3,4-dihydro-4-oxospiro[2H-1-benzopyran-2,1'-cyclohexan-7-yl)oxy}acetic acid To a solution of 2-{(5-methoxy-3,4-dihydro-4-oxospiro[2H-1-benzopyran-2,1'-cyclohexan-7 -yl)oxy}acetic acid (prepared in Example 21) (4.0 g, 12.5 mmol ) in acetonitrile (30 ml) is added 2N potassium hydroxide (7.5 ml, 15 mmol) and the mixture is stirred at room temperature for 2 hours. The solvent is removed under reduced pressure. The residue is mixed with ethanol and the mixture is filtered to separate potassium 2-{(5-methoxy-3,4-dihydro-4-oxospiro[2H-1-benzopyran-2,1'-cycl ohexan-7-yl)oxy}acetate as a crystalline solid (4.11 g, 92%). To a solution of the crystalline potassium salt (2.0 g, 5.6 mmol ) in dry DMF (20 ml) is added 1-iodomethyl pivalate (1.756 g, 7.25 mmol), and the mixture is stirred at room temperature for 3 hours and distilled under reduced pressure. To the residue is added ice-cold water and the mixture is extracted with ethyl acetate. The extract is dried and distilled under reduced pressure. The residue is purified by a silica gel column chromatography (eluent:dichloromethane and acetone, 20:1). The eluate is treated with a mixture of diethyl ether and hexane to obtain the title compound as a crystalline solid (2.0 g, 82.6%, m.p.=110°-111° C.).

Elemental analysis (for $C_{23}H_{30}O_8$)
Calcd.: C, 63.59; H, 6.96
Found: C, 63.58; H, 6.97
$^1$H-NMR (CDCl$_3$) δppm: 6.12(1H,d,J=2.4),
5.96(1H,d,J=2.4), 5.86(2H,s),
4.68(2H,s), 3.87(3H,s),
2.62(2H,s), 2.05–1.25(10H,m),
1.22(9H,s).

Example 57

1-(Pivaloyloxy)ethyl 2-{(5-methoxy-3,4-dihydro-4-oxospiro [2H-1-benzopyran-2,1'-cycl ohexan-7-yl)oxy} acetate To a solution of potassium 2-{(5-methoxy-3,4-dihydro-4-oxospiro[2H-1-benzopyran-2,1'-cyclo hexan-7-yl) oxy}acetate (prepared in Example 56) (0.50 g, 1.4 mmol) in dry DMF (5 ml) is added 1-iodoethyl pivalate (0.523 g, 1.68 mmol), and the mixture is stirred at room temperature for 0.5 hours and allowed to stand overnight at 5° C. The mixture is reacted at room temperature for additional one hour with stirring. The reaction mixture is then treated in a same manner as Example 56. Recrystallization from a mixture of diethyl ether and hexane gives the title compound as a crystalline solid (0.372 g, 59%, m.p.=121°-122° C.).

Elemental analysis (for $C_{24}H_{32}O_8 \cdot \frac{1}{4}H_2O$)
Calcd.: C, 63.63; H, 7.23
Found: C, 63.72; H, 7.10
$^1$H-NMR (CDCl$_3$) δppm: 6.91(1H,q,J=5.4),
6.09(1H,d,J=2.4),
5.97(1H,d,J=2.4), 4.63(2H,s),
3.86(3H,s), 2.61(2H,s),
2.05–1.10(10H,m),
1.49(3H,d,J=5.4), 1.18(9H,s).

Example 58

1-[(2-Cyclohexylacetyl)oxy]ethyl 2-[5-methoxy-3,4-dihydro-4-oxospiro[2H-1-benzopyran -2,1'-cyclohexan-7-yl) oxy]acetate To a solution of potassium 2-{(5-methoxy-3,4-dihydro-4-oxospiro [2H-1-benzopyran-2,1'-cycl ohexan-7-yl)oxy} acetate (prepared in Example 56) (0.50 g, 1.4 mmol) in dry DMF (5 ml) is added 1-chloroethyl cyclohexyl acetate (0.37 g, 1.81 mmol), and the mixture is stirred at 70° C. for 3 hours. The reaction mixture is treated in a same manner as Example 56 to yield the title compound as a thick syrup (0.343 g, 50%).

Elemental analysis (for $C_{27}H_{36}O_8$)
Calcd.: C, 66.38; H, 7.43
Found: C, 66.32; H, 7.58
$^1$H-NMR (CDCl$_3$) δppm: 6.92(1H,q,J=5.4),
6.08(1H,d,J=2.2),
5.96(1H,d,J=2.2), 4.60(2H,s),
3.85(3H,s), 2.59(2H,s),
2.17(2H,d,J=7.0),
2.00–0.80(21H,m),
1.50(3H,d,J=5.4).

Example 59

1-(Methoxycarbonyloxy)ethyl 2-[(5-methoxy-3,4dihydro-4-oxospiro[2H-1-benzopyran-2,1'-cyclohexan-7-yl)oxy]acetate To a solution of potassium 2-{(5-methoxy-3,4-dihydro-4-oxospiro[2H-1-benzopyran-2,1'-cyclo hexan-7-yl)oxy} acetate (prepared in Example 56) (0.50 g, 1.4 mmol) in dry DMF (5 ml) is added 1-chloroethyl methylcarbonate (0.232 g, 1.68 mmol). The mixture is stirred at room temperature for one hour, and then at 70° C. for one hour. The reaction mixture is treated in a same manner as Example 56. Recrystallization from a mixture of diethyl ether and hexane gives the title compound as a crystalline solid (0.234 g, m.p.=97°-98° C.).

Elemental analysis (for $C_{21}H_{26}O_9$)
Calcd.: C, 59.71; H, 6.20
Found: C, 59.74; H, 6.17
$^1$H-NMR (CDCl$_3$) δppm: 6.84(1H,q,J=5.4),
6.08(1H,d,J=2.3),
5.98(1H,d,J=2.3), 4.63(2H,s),
3.85(3H,s ), 3.79(3H,s),
2.60(2H,s), 2.00–1.20(10H,m),
1.54(3H,d,J=5.4).

Example 60

Phthalidyl 2-[(5-methoxy-3,4-dihydro-4-oxospiro [2H-1-benzopyran-2,1'-cyclohexan-7-yl)oxy]acetate To a solution of potassium 2-{(5-methoxy-3,4-dihydro-4-oxospiro[2H-1-benzopyran-2,1'-cyclo hexan-7-yl)oxy}acetate (prepared in Example 56) (2.18 g, 6.1 mmol) in dry DMF (20 ml) is added phthalidyl bromide (1.684 g, 7.9 mmol) and the mixture is stirred at room temperature for 7.5 hours, and distilled under reduced pressure. To the residue is added ice-cold water and the mixture is extracted with ethyl acetate. The extract is washed with water, dried, and distilled under reduced pressure. The resulting residue is purified by a silica gel column chromatography (eluent: dichloromethane and acetone, 20:1) to yield the title compound as a crystalline solid (1.394 g, 51%, m.p.=119°-120° C.).

Elemental analysis (for $C_{25}H_{24}O_8$)
Calcd.: C, 66.37; H, 5.35
Found: C, 66.07; H, 5.52
$^1$H-NMR (CDCl$_3$) δppm: 8.05–7.50(5H,m),
6.11(1H,d,J=2.2),
5.99(1H,d,J=2.2), 4.75(2H,s ),
3.86(3H,s), 2.64(2H,s),
2.10–1.20(10H,m).

Example 61

1,5-Dihydro-1-{2-[(5-methoxy-3,4-dihydro-4-oxospiro[2H-1-benzopyran-2,1'-cyc lohexan-7-yl)oxy] acetyloxymethyl}-4H-pyrazolo[3,4-d]pyrimidin-4-one To a mixture of 2-{(5-methoxy-3,4-dihydro-4-oxospiro[2H-1-benzopyran-2,1'-cyclohexan-7 -yl)oxy}acetic acid (prepared in Example 21) (0.960 g, 3.0 mmol), triphenylphosphine (0.944 g, 3.6 mmol), 1,5-dihydro-1-hydroxymethyl-4H-pyrazolo[3,4-d]pyrimidin-4-one [P.C.Bausal, I.H.Pitman, and T.Higuchi, J.Pharm.Sci., 70, 855, (1981)] (0.548 g, 3.3 mmol) in dry dioxane (20 ml) is added a solution of diethyl azodicarboxylate (0.626 g, 3.6 mmol) in dioxane (10 ml). After 3 days stirring at room temperature, diethyl azodicarboxylate (0.104 g, 0.6 mmol) is added to it and the mixture is stirred for additional 2 hours. The mixture is distilled under reduced pressure and the residue is purified by a silica gel column chromatography (eluent: dichloromethane and methanol, 20:1). Recrystallization from ethyl acetate gives the title compound as a crystalline solid (1.0 g, 70%, m.p.=139°–141 °C.).

Elemental analysis (for $C_{23}H_{24}N_4O_7 \cdot \frac{1}{2}H_2O$)
Calcd.: C, 57.86; H, 5.28; N, 11.73
Found: C, 57.70; H, 5.08; N, 11.84
1H-NMR (d$_6$-DMSO) δppm: 12.45(1H,s), 8.21(1H,s), 8.18(1H,s), 6.35(2H,s),
6.14(1H,d,J=2.2),
6.04(1H,d,J=2.2),
4.94(2H,s), 3.72(3H,s),
2.56(2H,s ), 1.85–1.25(10H,m).

The following experiments were conducted to demonstrate the ability of the compounds of the present invention in the acceleration of the excretion of uric acid and inhibition of xanthine oxidase which leads to inhibition of biosynthesis of uric acid.

Experiment 1

Accelerated uric acid clearance in rats caused by administration of compound (I).

a) Method

Nine-week-old male rats were employed for the test. As a pre-treatment for measuring uric acid clearance and inulin clearance, each animal was anesthetized with pentobarbital sodium, and canulae were placed into the right femoral artery (for blood collection), left femoral vein (for drug infusion), and urinary bladder (for urine collection) of each animal. 60% Urethane was subcutaneously administered to each animal at a dose of 2 ml/kg body weight and then 1.7% potassium oxonate/1.5% inulin/4% mannitol/0.9% saline solution was intravenously administered. After that, 0.5% pottasium oxonate/4% mannitol/1.5% inulin/0.9% saline was infused to each animal at a flow rate of 0.05 ml per minute on a hot plate kept at 30° C. Thirty minutes later, 0.9% saline was intraperitonealy administered at 4 ml/kg body weight. After the equilibrium for another 30 minutes, arterial blood (0.2 ml each) samples were collected 6 times at every 20 minute interval and five 20-minute urine samples were collected. Immediately after the collection of every blood sample, the serum was separated therefrom, and the serum samples and the urine samples were stored in a refrigerator.

Immediately after the first collection of the urine sample, the test compound suspended in 1% gum arabic was intraperitoneally administered at 2 ml/kg body weight.

Uric acid both in the serum and in the urine was quantitatively analyzed by the method of Yonetani et al's. [Yonetani, Y.; Ishii, M.; Iwaki, K., Japanese J. Pharmacology 30, 829–840 (1980).] Inulin was also done substantially by the method of Vurek's and Pegram's [Vurek, G G., Pegram, S.E., Anal.Biochem., 16, 409–419 (1966)]. In order to analyze uric acid, 0.2 ml of diluted solution of deproteinized serum or urine was admixed with 2.5 ml of 0.4% dimedon/orthphosphoric acid solution and the resulting mixture was heated in a hot bath for 5 minutes. The mixture was then cooled in ice-cold water and the fluorescence was measured at 400 nm in the excitation wave length at 360 nm. Control experiments were carried out using an equivalent amount of positive control compounds, ([5-chloro-3-(2-methylphenyl)-4-oxo-4H-1-benzopyran-7-yl] oxy)acetic acid and benzbromarone.

b) Results

The results are listed in Table 11, showing that the ability of compounds of the present invention in accelerating the excretion of uric acid is superior or equivalent to that of each of the control compounds.

TABLE 11

| Example No. of Compound | dose (mg/kg) | ΔUuaV[a] (mg/kg-min) | FEua[b] |
|---|---|---|---|
| 11 | 10 | 0.022 | 0.061 |
| 21 | 10 | 0.046 | 0.110 |
| 22 | 10 | 0.029 | 0.128 |
| 23 | 10 | 0.051 | 0.160 |
| 24 | 10 | 0.024 | 0.096 |
| 25 | 10 | 0.043 | 0.088 |
| 30 | 10 | 0.036 | 0.128 |
| 33 | 50 | 0.047 | 0.142 |
| 34 | 10 | 0.040 | 0.096 |
| 49 | 10 | 0.082 | 0.182 |
| 54 | 10 | 0.039 | 0.129 |
| 61 | 25 | −0.006 | 0.103 |
| control[c] | 10 | — | 0.081 |
| control[d] | 10 | 0.068 | 0.125 | a) Increment of urinary uric acid was calculated by subtracting the control value from the mean value of four measurements after the administration of test compound.

b) Increment of fractional excretion of uric acid [Uric acid clearance/inulin clearance (i.e., glomerular filtration rate)] was calculated by subtracting the control value from the mean value of four measurements after the administration of test compound.

c) ([5-chloro-3-(2-methylphenyl)-4-oxo-4H-1-benzopyran-7-yl]oxy)acetic acid d) Benzbromarone Experiment 2

Evaluation of xanthine oxidase inhibition activity

A mixture of 0.05M phosphate buffer (pH=8, 2 ml), $5.0 \times 10^{-4}$M xanthine solution (0.5 ml), and an aqueous solution of a test compound (0.3 ml) was charged in a cell for the spectrophotometer. An aqueous solution of xanthine oxidase (200 times dilution, Böelinger Manheim, milk xanthine oxidase) (0.2 ml) was added to the mixture. The absorbance at 293 nm was measured before, and 10 minutes after, the addition of xanthine. The increase in the two measurements is attributable to the amount of synthesized uric acid. Control experiment was carried out using water instead of the test compound solution. The 50% inhibition rate (IC$_{50}$) was determined by assuming the increment obtained in the control trial to 100.

The results are shown below:

| Test compound | IC$_{50}$ (M) |
|---|---|
| Compound prepared in Example 21: | $6.5 \times 10^{-5}$ |
| Allopurinol: | $1.6 \times 10^{-6}$ |

The results of Experiments 1 and 2 demonstrate that the compounds of the present invention can accelerate the excretion of uric acid and also inhibit the biosynthesis of uric acid through xanthine oxidase inhibition activity.

Therefore, the compounds of the invention are effective for the treatment of various disorders associated with elevated uric acid levels, including hyperuricemia, gout, ischemic cardiac diseases, cerebrovascular diseases, and the like.

For the treatment or prophylaxis of the diseases noted above, a selected compound of the formula (I) is administered to a patient suffering from any of these disorders in amount effective to reduce uric acid levels or treat said disorders.

The compounds may be administered either orally or parenterally in the form of an appropriate pharmaceutical composition. The compositions can be in the form of tablets, granules, fine granules, powders, capsules, injectable solutions (for intravenous or intramuscular injection), and the like. The daily oral dosage for adult can be from about 0.5 to about 300 mg/kg, preferably about 5 to about 100 mg/kg, while the daily parenteral dosage can range from about 0.15 to about 100 mg/kg, preferably about 1 to about 50 mg/kg. The dose can be administered at a time or several times after appropriately divided.

What is claimed is:

1. A method for treating hyperuricemia which comprises administering to a patient suffering from said disease an effective amount of a compound of the formula (I):

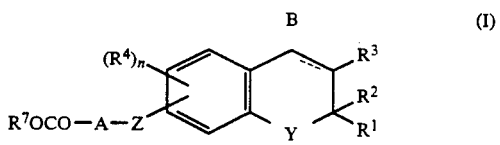

wherein:
- $R^1$ and $R^2$ form a four- to eight-membered carbon ring together with the carbon atom to which they are attached;
- $R^3$ is hydrogen of $C_1$ to $C_5$ lower alkyl;
- n is 1 or 2;
- when n is 1, $R^4$ is a radical selected from the group consisting of hydrogen, halogen, nitro, $C_1$ to $C_5$ lower alkyl, phenyl, phenyl substituted with halogen or $C_1$ to $C_5$ lower alkyl, $-OR^5$ and $-SO_2NR^6R^{6'}$, when n is 2, $(R^4)_2$ represents two radicals independently selected from the group consisting of hydrogen, halogen, nitro, $C_1$ to $C_5$ lower alkyl, phenyl, phenyl substituted with halogen or $C_1$ to $C_5$ lower alkyl, $-OR^5$ and $-SO_2NR^6R^{6'}$;
- $R^5$ is hydrogen, $C_1$ to $C_5$ lower alkyl, $C_1$ to $C_5$ lower alkyl substituted with phenyl, carboxymethyl, $C_1$ to $C_5$ lower alkyl ester of carboxymethyl, hydroxyethyl, benzyl, or allyl;
- $R^6$ and $R^{6'}$ are independently hydrogen or $C_1$ to $C_5$ lower alkyl;
- $R^7$ is hydrogen or an ester-forming group selected from the group consisting of acetoxymethyl, acetoxyethyl, propionyloxymethyl, pivaloyloxymethyl, pivaloyloxyethyl, cyclohexaneacetoxyethyl, cyclohexanecarbonyloxycyclohexylmethyl and phthalidyl;
- A is a straight or branched hydrocarbon radical having one to five carbon atoms;
- B is halogen, oxygen, or ethylenedithio;
- Y is oxygen;
- Z is oxygen, nitrogen or nitrogen substituted with hydrogen, $C_1$ to $C_5$ lower alkyl, or acetyl; and
- the symbol ▭ shown within the ring structure means a single bond or a double bond, the symbol ▭ associated with B means a single bond, a double bond or, in the case where B is ethylenedithio, two single bonds.

2. A method as claimed in claim 1 wherein Z is oxygen, A is methylene and $R^4$ is $-OR^5$.

3. A method as claimed in claim 1 wherein B is oxygen.

4. A method as claimed in claim 2 wherein B is oxygen.

5. A method as claimed in claim 1 wherein the compound of the formula (I) is {(5-methoxy-3,4-dihydro-4-oxospiro[2H-1-benzopyran-2,1'-cyclohexan]-7-yl)oxy}-acetic acid or a pharmaceutically active ester thereof formed with an ester-forming group selected from the group consisting of acetoxymethyl, acetoxyethyl, propionyloxymethyl, pivaloyloxymethyl, pivaloyloxyethyl, cyclohexaneacetoxyethyl, cyclohexanecarbonyloxycyclohexylmethyl and phthalidyl.

* * * * *